United States Patent
Miklatzky et al.

(10) Patent No.: US 10,863,816 B2
(45) Date of Patent: Dec. 15, 2020

(54) METHOD AND SYSTEM FOR CUSTOMIZED HAIR-COLORING

(71) Applicant: COLORIGHT LTD., Rehovot (IL)

(72) Inventors: Efraim Miklatzky, Neve Ilan (IL); Sagiv Lustig, Ramat Hasharon (IL); Elena Ishkov, Rehovot (IL); Eliyahu Benny, Rehovot (IL); Hila Sela, Ramle (IL); Roy Frenkel, Kfar Menachem (IL)

(73) Assignee: COLORIGHT LTD., Rehovot (IL)

( * ) Notice: Subject to any disclaimer, the term of this patent is extended or adjusted under 35 U.S.C. 154(b) by 361 days.

(21) Appl. No.: 15/770,549

(22) PCT Filed: Nov. 4, 2016

(86) PCT No.: PCT/IB2016/056649
§ 371 (c)(1),
(2) Date: Apr. 24, 2018

(87) PCT Pub. No.: WO2017/077498
PCT Pub. Date: May 11, 2017

(65) Prior Publication Data
US 2019/0059560 A1    Feb. 28, 2019

Related U.S. Application Data

(60) Provisional application No. 62/251,099, filed on Nov. 4, 2015.

(51) Int. Cl.
A45D 44/00     (2006.01)
A45D 19/00     (2006.01)
(Continued)

(52) U.S. Cl.
CPC ....... A45D 44/005 (2013.01); A45D 19/0008 (2013.01); G01J 3/50 (2013.01);
(Continued)

(58) Field of Classification Search
CPC .............. A45D 44/005; A45D 19/0008; A45D 2019/0066; A45D 2044/007;
(Continued)

(56) References Cited

U.S. PATENT DOCUMENTS 7,877,294 B2 * 1/2011 Inzinna, Jr. ............... G01J 3/46
                                                       705/26.1
9,316,580 B2 * 4/2016 Landa .................... G01N 21/27
(Continued)

FOREIGN PATENT DOCUMENTS

CN     1339947 A    3/2002
CN     1440503 A    9/2003
(Continued)

OTHER PUBLICATIONS

Japanese Office Action dated Jul. 16, 2019 in Japanese Patent Application No. 2018-522945, 4 pages.
(Continued)

*Primary Examiner* — Michael Collins
(74) *Attorney, Agent, or Firm* — Oblon, McClelland, Maier & Neustadt, L.L.P.

(57) ABSTRACT

Systems and methods for computing a hair-coloring composition (HCC) or for dispensing ingredients for the HCC are disclosed herein. In some embodiments, the system comprises a hair-treatment objective-prioritization user interface (HTOP UI) for receiving multi-objective relative-importance data describing a relative importance of different hair-treatment objectives (e.g. immediate post-treatment accuracy versus auxiliary goals, or one auxiliary goal versus another) for a potential hair-coloring treatment. In some embodiments, a hair-coloring-composition (HCC) prediction-engine is responsive to input received via the HTOP UI to compute, from the initial hair-state data and from the target color-state, a customized hair-coloring composition (Continued)

predicted to transform a color state of the user's hair from the initial color state to the target color state. This may be performed according to the multi-objective relative-importance data.

8 Claims, 34 Drawing Sheets

(51) Int. Cl.
  *G01J 3/50* (2006.01)
  *G16H 20/70* (2018.01)
  *G01J 3/46* (2006.01)
(52) U.S. Cl.
  CPC ..... *G16H 20/70* (2018.01); *A45D 2019/0066* (2013.01); *A45D 2044/007* (2013.01); *A45D 2200/058* (2013.01); *G01J 2003/467* (2013.01)
(58) Field of Classification Search
  CPC ..... A45D 2200/058; G16H 20/70; G01J 3/50; G01J 2003/467
  USPC .................................. 700/231–244
  See application file for complete search history.

(56) References Cited

U.S. PATENT DOCUMENTS

| | | | |
|---|---|---|---|
| 10,012,588 B2* | 7/2018 | Miklatzky | G01J 3/463 |
| 10,292,482 B2* | 5/2019 | Miklatzky | G01N 21/84 |
| 10,302,495 B2* | 5/2019 | Miklatzky | G01J 3/0272 |
| 10,416,078 B2* | 9/2019 | Miklatzky | G01J 3/0264 |
| 2002/0010556 A1 | 1/2002 | Marapane et al. | |
| 2004/0210661 A1 | 10/2004 | Thompson | |
| 2006/0033907 A1 | 2/2006 | Inzinna, Jr. | |
| 2006/0195300 A1 | 8/2006 | Grossinger et al. | |
| 2014/0082854 A1* | 3/2014 | Landa | G01N 33/4833 8/405 |
| 2014/0094964 A1* | 4/2014 | Bartholomew | G07F 11/56 700/233 |
| 2015/0089751 A1* | 4/2015 | Landa | B65D 1/0223 8/406 |

FOREIGN PATENT DOCUMENTS

| | | |
|---|---|---|
| EP | 2 133 673 A1 | 12/2009 |
| JP | 2014-510099 A | 4/2014 |
| WO | WO 2009/152033 A1 | 12/2009 |
| WO | WO 2015/166340 A2 | 11/2015 |

OTHER PUBLICATIONS

Office Action dated Aug. 13, 2020 in Chinese Application No. 201680077821.2.
International Search Report and Written Opinion dated Apr. 6, 2017 in PCT/IB2016/056649 filed Nov. 4, 2016.
Combined Chinese Office Action and Search Report dated Jan. 2, 2020 in Chinese Patent Application No. 201680077821.2 (with English translation of Category of Cited Documents), 9 pages.
Extended European Search Report dated May 21, 2019 in European Patent Application No. 16861713.2, 11 pages.
European Office Action dated Jun. 7, 2019 in European Patent Application No. 16861713.2, 1 page.
Korean Office Action dated May 28, 2019 in Korean Patent Application No. 10-2018-7015727 (with English translation), 7 pages.

* cited by examiner

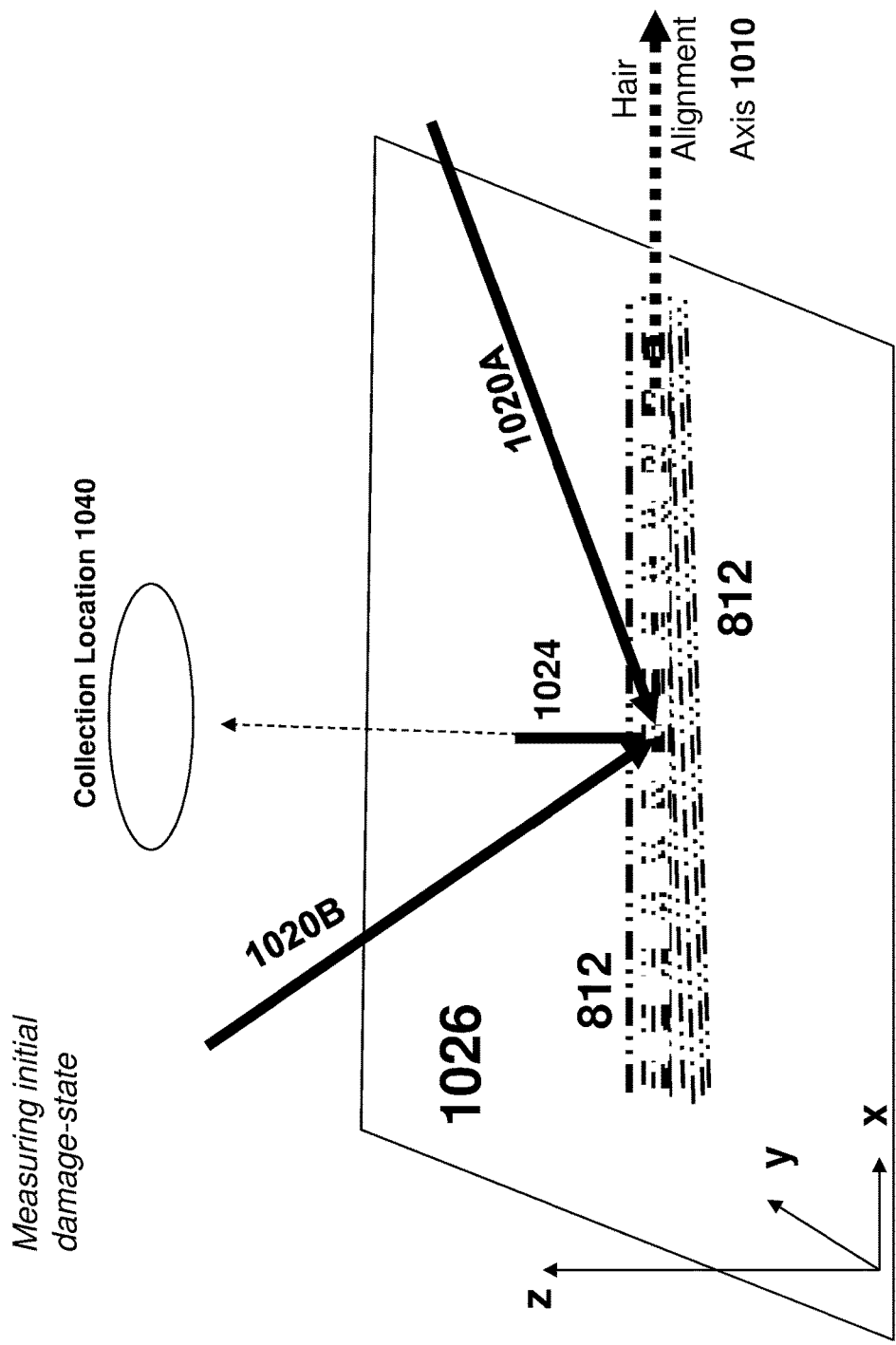

METHOD AND SYSTEM FOR CUSTOMIZED HAIR-COLORING

CROSS-REFERENCE TO RELATED APPLICATIONS

This patent application claims the benefit of U.S. Provisional Patent Application No. 62/251,099 filed on Nov. 4, 2015 which is incorporated by reference in its entirety.

BACKGROUND

Hair Coloring

Hair-coloring has been practiced for millennia, and continues to play an important in modern society. A central problem in the art of hair-coloring is to provide the correct treatment—e.g. the appropriate hair-coloring composition and/or treatment parameters (e.g. treatment time, temperature, etc).

PCT/IB2012/051351 discloses a dispensing device comprising a plurality of containers, where each container contains a different respective ingredient for a hair-coloring composition. An initial spectrum of the hair is measured and analyzed. In accordance with the results of the analysis, a combination of ingredients for a customized hair-coloring composition (i.e. specific to the user's hair and a desired result to be achieved) is dispensed from the containers by a dispensing device.

The combination of ingredients for the hair-coloring composition is selected according to analysis of a measured hair-spectrum. Therefore, it is highly desirable to accurately measure the initial spectrum of the hair-sample, in order to provide the customized hair-coloring best suited to the user's hair and his/her hair-coloring goals.

Predicting the Results of a Hypothetical Hair-Color Treatment by a Hypothetical Hair Coloring Composition (HCC) (FIG. 1)

It is known in the art to predict an immediate post-coloring state—i.e. to predict a color of hair immediately after hair-coloring treatment. The immediate post-treatment state of the hair may be computed from (i) data describing color properties of 'initial hair' (i.e. colorimetric or spectral data) and (ii) data describing the hair-coloring composition HCC (e.g. concentrations of one or more artificial colorants in the hair-coloring composition).

Towards this end, the pre-hair-coloring-treatment color state of the hair is characterized or measured (e.g. by acquiring colorimetric or spectral data). The color state data (e.g. colorimetric or spectral data) may be expressed for example, in color-space (e.g. in LAB color coordinates) or as a spectra(um) (e.g. reflection or transmission or absorption spectra) or in any other manner known in the art of colorimetry. Various examples of the present disclosure relate to 'color coordinates'—this is intended to generically/schematically describe any color-state and may relate to colorimetric or spectral data or any other known description of color-state.

For example, PCT/IB2012/051351 filed on Mar. 21, 2012 discloses measuring an initial spectrum of the 'initial hair' (i.e. before the hair-coloring treatment) presence concentrations of keratin, eumelanin, pheomelanin and/or artificial pigments. In this example, if concentrations of dye(s) of the HCC are known, it is possible to (i) compute a predicted concentration of natural and artificial colorants in the hair after the dying (e.g. oxidative hair-dying) process; and (ii) compute from the predicted colorant concentrations a predictive post-hair-coloring treatment spectrum (e.g. reflection or absorption spectrum), representing the post-treatment color state. FIG. 1 schematically illustrates first and second color coordinate—they may be features of the pre-treatment and post-treatment spectra.

FIG. 1 schematically illustrates computing a prediction of post-treatment color state of initial hair—i.e. the predicted color state of the hair immediately after subjecting the initial hair to the hair-coloring treatment.

Computing a Hair-Coloring Treatment (FIGS. 2A-2B and 3) It is known in the art of hair-coloring to measure an initial color state of a user's hair, and to solicit a target color state describing a desired hair-color for the user's hair. For example, a person with black hair desires a particular shade of red, a person with gray hair desires a particular shade of blond, and so on. Based upon this information, it is possible to compute a hair coloring composition (HCC) that is predicted to transform the user's hair to the target color state. This is shown in FIG. 2A.

One implementation for achieving this is shown in FIG. 2B. In particular, a data describing a number of candidate HCCs may be generated, and for each of the candidate HCC, a respective predicted target state is computed. In the example of FIG. 2B, predicted computed states are computed for four candidate HCCs—HCC cand1, HCC cand2, HCC cand3, and HCC cand4.

In order to 'compute' the hair coloring treatment, a respective deviation between the target color state and the predicted post-treatment color state for each HCC is computed. As shown in FIG. 3, once the deviations are computed, the 'best' (or highest scoring) candidate is selected to be that whose corresponding post-treatment color state is predicted to have the smallest deviation (i.e. a post-treatment color states) from the target color state.

It is possible to operatively couple a 'HCC computation' engine that employs this greedy approach to a multi-container dispensing device. A different hair-coloring agent is stored within each container—the computed HCC specifies relative quantities of each agent. Agents may be dispensed from each container in quantities determined by the computed HCC, and in response to the computing of the HCC.

Gray Hair

Embodiments of the present invention relate to methods and apparatus for analyzing "natural gray hair"—e.g. in order to provide a customized hair-coloring composition suitable for the natural gray hair.

For a significant segment of the population, as people age, their hair grays, and their hair becomes 'natural gray.' 'Natural gray hair' may be distinguished from 'artificial gray' hair, where a presence of artificial colorant gives individual hair-shafts their gray color.

Natural gray hair is a mixture of two types of hair-shafts: (i) natural-pigment-containing hair shafts (e.g. melanin-containing hair shafts such as black shafts or red shafts or blond shafts or brown shafts or other natural-pigment-containing shafts) and (ii) natural white hair shafts which are substantially melanin-free e.g. due to age. The presence of both color-types of hair-shafts within a single hair-mixture causes the mixture as a whole to appear as 'gray hair' to the casual naked-eye viewer.

For the present disclosure, the term 'shaft' refers to an individual hair and is not limited to the 'shaft portion' (i.e. away from the root portion) of an individual hair.

Natural gray hair is one example, but not the only example, of a shaft-color-heterogeneous 'mixture' of hair-shafts also referred to herein as 'a color-heterogeneous mixture of hair.'

Sometimes, natural gray hair is subjected to a 'hair-coloring treatment' which may change the overall appearance so it is no longer considered 'natural gray.' For the present disclosure, a 'hair-coloring treatment' is any treatment which modifies the color of hair shafts. Examples of hair-coloring treatments include hair-dying treatments (e.g. based upon artificial colorants) and bleaching. Hair-dying treatments include temporary, demi-permanent, semi-permanent or permanent hair-dying (e.g. oxidative hair-dying) treatments.

For the present disclosure, 'formerly natural gray hair' is mixture of hair that (i) in the past was "natural gray" but has been transformed by a hair-coloring treatment and (ii) is presently recognizable (e.g. upon inspection by a hair-stylist or other skilled artisan) to have properties indicative of its former status as naturally grey hair. In one example, a mixture of natural black and natural white hair-shafts (i.e. one type of natural gray hair) is artificially dyed red—e.g. by an oxidative hair-dying process.

In this example, as a result of the red hair-dye treatment, each natural white hair-shaft becomes a relatively light shade of red, while each natural black hair shaft become a darker shade of red—this is observable upon close inspections of the individual hair shafts. In contrast, the overall appearance of the mixture (i.e. as whole) differs from that of the individual shafts (i.e. viewed in isolation).

In this example, before treatment with the red dye, the hair is natural-gray and is a mixture of natural-black and natural white hair-shafts. After the hair-dying process, the hair is 'formerly-natural-gray' and is a mixture of hair-shafts of first and second color-types. The hair shafts of the first color type are the shafts that, before the dying process, are natural black—after the dying process, these hair-shafts are dark red. The hair shafts of the second color type are the shafts that, before the dying process, are natural white—after the dying process, these hair-shafts are light red.

The following issued patents and patent publications provide potentially relevant background material, and are all incorporated by reference in their entirety: US 20080068604, US 20060195300, US 20040000015, U.S. Pat. No. 707,929, WO/2012/127429 and WO/2010/004565.

SUMMARY OF EMBODIMENTS

A system for preparing a customized hair-coloring composition by dispensing material comprising: a hair-treatment objective-prioritization user interface (HTOP UI) for receiving multi-objective relative-importance data describing a relative importance of different hair-treatment objectives for a potential hair-coloring treatment; a hair-state circuit configured to store a target color state for the potential hair-coloring treatment and initial hair-state data describing at least an initial color-state of the user's hair before being subjected to the potential hair-coloring treatment; and a hair-coloring-composition (HCC) prediction-engine responsive to input received via the HTOP UI, the hair-coloring-composition prediction-engine configured to compute, from the initial hair-state data and from the target color-state, a customized hair-coloring composition predicted to transform a color state of the user's hair from the initial color state to the target color state; wherein: the HTOP UI is configured so that the multi-objective relative-importance data describes a relative importance of (A) reaching the target color-state; and (B) achieving at least one auxiliary objective(s) or achieving a user-specified weighted combination of auxiliary objective(s); in response to receipt, via the HTOP UI, of multi-objective relative-importance data that prioritizes immediate-post-treatment color-state accuracy at the expense of achieving the auxiliary objective, the HCC prediction-engine computes a hair-coloring composition predicted to more accurately transform the user's hair to the target color state at the expense of achieving the auxiliary objective; and in response to receipt, via the HTOP UI, of multi-objective relative-importance data that prioritizes achieving the auxiliary objective at the expense of predicted immediate-post-treatment color-state accuracy, the HCC prediction-engine computes a hair-coloring composition that achieves the auxiliary objective at the expense of immediate-post-treatment color-state accuracy.

A system for preparing a customized hair-coloring composition by dispensing material, the system comprising: a hair-treatment objective-prioritization user interface (HTOP UI) for receiving multi-objective relative-importance data describing a relative importance of different hair-treatment objectives for a potential hair-coloring treatment; a hair-state circuit configured to store a target color state for the potential hair-coloring treatment and initial hair-state data describing at least an initial color-state of the user's hair before being subjected to the potential hair-coloring treatment; and a dispenser device having a plurality of containers, a different material being respectively disposed in each container, the dispenser device configured to respectively dispense a different quantity of material from each container in response to and according to computations performed by a digital computer; wherein: in response to receipt, via the HTOP UI, of multi-objective relative-importance data that prioritizes immediate-post-treatment color-state accuracy at the expense of achieving the auxiliary objective, the dispenser device dispenses materials from the containers at relative quantities for a hair-coloring composition that more accurately transforms the user's hair to the target color state at the expense of achieving the auxiliary objective; and in response to receipt, via the HTOP UI, of multi-objective relative-importance data that prioritizes achieving the auxiliary objective at the expense of immediate-post-treatment color-state accuracy, the dispenser device dispenses materials from the containers at relative quantities for a hair-coloring composition that achieves the auxiliary objective at the expense of immediate-post-treatment color-state accuracy.

In some embodiments, at least one of the auxiliary objectives is post-treatment color-retaining wash-robustness.

In some embodiments, at least one of the auxiliary objectives is achieving uniform color-state between initial hair-shafts of different colors.

In some embodiments, at least one of the auxiliary objectives is minimizing a post-treatment damage state and/or predicting that the post-treatment damage state does not exceed a threshold.

In some embodiments, at least one of the auxiliary objectives is minimizing a treatment complexity.

A method of computing a hair-coloring composition that is customized for a user's hair and for a target hair-color state, the hair-coloring composition comprising a plurality of artificial colorants, the method comprising: receiving initial hair-state data describing an initial color-state of the user's hair and optionally auxiliary hair-state data of the user's hair; performing an optimized hair-dispensing of ingredients selected from a plurality of ingredients a plurality of candidate ingredients at relative quantities that are multi-goal-optimized for at least the following two at least partially-contradicting goals: transforming the hair from the initial color-state to the target color state and providing a hair-coloring composition that has an optimal wash-robustness.

A method of computing a hair-coloring composition that is customized for a user's hair and for a target hair-color state, the hair-coloring composition comprising a plurality of artificial colorants, the method comprising: receiving initial hair-state data describing an initial color-state of the user's hair and optionally auxiliary hair-state data of the user's hair; for each candidate hair-coloring composition of a plurality of candidates, respectively computing from the initial hair-state data: a predicted immediate-post-treatment color-state of the user's hair following coloring the user's hair by the candidate hair-coloring composition; and a predicted color-retention of the user hair following post-treatment washing(s) of the user's hair after coloring by the candidate hair-coloring composition; scoring each candidate hair-coloring composition according to competing scoring criteria such that: score of a candidate increases (decreases) as a candidate-specific predicted color-deviation between the target color state and the candidate-specific immediate-post-treatment color state decreases (increases); and a score of the hair-coloring composition increases (decreases) as the predicted color-retention improves, wherein the predicted color-retention is computed according to a plurality of colorant concentration-decay curves, one for each artificial colorant.

In some embodiments, the concentration-decay curves are damage-dependent to depend upon a predicted post-treatment damage-state of the user's hair.

In some embodiments, the auxiliary hair-state data includes a pre-treatment damage-state of the hair.

In some embodiments, the auxiliary hair-state data includes a thickness of the hair.

A system for preparing a customized hair-coloring composition by dispensing material, the system comprising: a hair-treatment objective-prioritization user interface (HTOP UI) for receiving multi-objective relative-importance data describing a relative importance of different hair-treatment objectives for a potential hair-coloring treatment; a hair-state circuit configured to store a target color state for the potential hair-coloring treatment and initial hair-state data describing at least an initial color-state of the user's hair before being subjected to the potential hair-coloring treatment; and a hair-coloring-composition (HCC) prediction-engine responsive to input received via the HTOP UI, the hair-coloring-composition prediction-engine configured to compute, from the initial hair-state data and from the target color-state, a customized hair-coloring composition predicted to transform a color state of the user's hair from the initial color state to the target color state; wherein: the HTOP UI is configured so that the multi-objective relative-importance data describes a relative importance of (A) reaching the target color-state; and (B) achieving at least one auxiliary objective(s) or achieving a user-specified weighted combination of auxiliary objective(s); in response to receipt, via the HTOP UI, of multi-objective relative-importance data that prioritizes the first auxiliary objective the expense of the second auxiliary objective, the hair-coloring-composition (HCC) prediction engine computes a hair-coloring composition that is predicted to achieve the first auxiliary objective at the expense of the second auxiliary objective; and in response to receipt, via the HTOP UI, of multi-objective relative-importance data that prioritizes the second auxiliary objective the expense of the first auxiliary objective, the hair-coloring-composition (HCC) prediction engine computes a hair-coloring composition that is predicted to achieve the second auxiliary objective at the expense of the first auxiliary objective.

A system for preparing a customized hair-coloring composition by dispensing material, the system comprising: a hair-treatment objective-prioritization user interface (HTOP UI) for receiving multi-objective relative-importance data describing a relative importance of different hair-treatment objectives for a potential hair-coloring treatment; a hair-state circuit configured to store a target color state for the potential hair-coloring treatment and initial hair-state data describing at least an initial color-state of the user's hair before being subjected to the potential hair-coloring treatment; and a dispenser device having a plurality of containers, a different material being respectively disposed in each container, the dispenser device configured to respectively dispense a different quantity of material from each container in response to and according to computations performed by a digital computer; wherein: in response to receipt, via the HTOP UI, of multi-objective relative-importance data that prioritizes the first auxiliary objective the expense of the second auxiliary objective, the dispenser device dispenses materials from the containers at relative quantities for a hair-coloring composition that is predicted to achieve the first auxiliary objective at the expense of the second auxiliary objective; and in response to receipt, via the HTOP UI, of multi-objective relative-importance data that prioritizes the second auxiliary objective the expense of the first auxiliary objective, the dispenser device dispenses materials from the containers at relative quantities for a hair-coloring composition that is predicted to achieve the second auxiliary objective at the expense of the first auxiliary objective.

In some embodiments, the first of the auxiliary objectives is last and the second of the auxiliary objective is gentleness.

In some embodiments, the first of the auxiliary objectives is uniformity/coverage and the second of the auxiliary objective is gentleness.

In some embodiments, the first of the auxiliary objectives is last and a second of the auxiliary objective is uniformity/coverage.

In some embodiments, the first of the auxiliary objectives is any first objective described herein and the second of the auxiliary objective is any second objective described herein.

In some embodiments, the target color state and/or the initial hair-state data comprises at least one of spectral data and colorimetric data.

In some embodiments, the spectral data comprises at least one of a reflection spectrum, a transmission spectrum and an absorption spectrum.

Some embodiments relate to a system for preparing a customized hair-coloring composition by dispensing material, the system comprising: a. computer storage for storing (i) a target color state and (ii) initial hair-state data describing at least an initial color-state of the user's hair; b. a computation-engine configured to compute, from the initial hair-state data and from the target color-state, a customized hair-coloring composition predicted to transform a color state of the user's hair from the initial color state towards (e.g. approximately to or exactly to) the target color state; and c. a user interface for receiving multi-objective relative-importance data describing a relative importance of (i) reaching the target color-state; and (ii) achieving at least one auxiliary objective(s) or achieving a user-specified weighted combination of auxiliary objective(s), wherein: i. in response to receipt of multi-objective relative-importance data that prioritizes immediate-post-treatment color-state accuracy at the expense of achieving the auxiliary objective, the computation engine computes a hair-coloring composition that more accurately transforms the user's hair towards the target color state at the expense of achieving the auxiliary objective; and ii. in response to receipt of multi-objective relative-importance data that prioritizes achieving the auxiliary objective at the expense of immediate-post-treatment color-state accuracy, the computation engine computes a hair-coloring composition that better achieves the auxiliary objective at the expense of immediate-post-treatment color-state accuracy.

Some embodiments relate to system for preparing a customized hair-coloring composition by dispensing material, the system comprising: a. computer storage for storing (i) a target color state and (ii) initial hair-state data describing at least an initial color-state of the user's hair; b. a user interface for receiving multi-objective relative-importance data describing a relative importance of (i) reaching the target color-state; and (ii) achieving at least one auxiliary objective(s) or achieving a user-specified weighted combination of auxiliary objective(s), c. a dispenser device having a plurality of containers, a different material being respectively disposed in each container, the dispenser device configured to respectively dispense a different quantity of material from each container in response to and according to computations performed by a digital computer; wherein: i. in response to receipt of multi-objective relative-importance data that prioritizes immediate-post-treatment color-state accuracy at the expense of achieving the auxiliary objective, the dispenser device dispenses materials from the containers at relative quantities for a hair-coloring composition that more accurately transforms the user's hair towards the target color state at the expense of achieving the auxiliary objective; and ii. in response to receipt of multi-objective relative-importance data that prioritizes achieving the auxiliary objective at the expense of immediate-post-treatment color-state accuracy, the dispenser device dispenses materials from the containers at relative quantities for a hair-coloring composition that better achieves the auxiliary objective at the expense of immediate-post-treatment color-state accuracy.

In some embodiments, at least one of the auxiliary objectives is post-treatment color-retaining wash-robustness—e.g. 'last.'

In some embodiments, at least one of the auxiliary objectives is achieving uniform color-state between initial hair-shafts of different colors—e.g. coverage.

In some embodiments, at least one of the auxiliary objectives is minimizing a post-treatment damage state and/or predicting that the post-treatment damage state does not exceed a threshold.

In some embodiments, at least one of the auxiliary objectives is minimizing a treatment complexity (e.g. number of steps of the treatment).

Some embodiments relate to a method of computing a hair-coloring composition that is customized for a user's hair and for a target hair-color state, the hair-coloring composition comprising a plurality of artificial colorants, the method comprising: a. receiving initial hair-state data describing an initial color-state of the user's hair and optionally auxiliary hair-state data of the user's hair; b. performing an optimized hair-dispensing of ingredients selected from a plurality of ingredients a plurality of candidate ingredients at relative quantities that are multi-goal-optimized for at least the following two at least partially-contradicting goals: (i) transforming the hair from the initial color-state to the target color state and (ii) providing a hair-coloring composition that has an optimal wash-robustness.

Some embodiments relate to a method of computing a hair-coloring composition that is customized for a user's hair and for a target hair-color state, the hair-coloring composition comprising a plurality of artificial colorants, the method comprising: a. receiving initial hair-state data describing an initial color-state of the user's hair and optionally auxiliary hair-state data of the user's hair; b. for each candidate hair-coloring composition of a plurality of candidates, respectively computing from the initial hair-state data: i. a predicted immediate-post-treatment color-state of the user's hair following coloring the user's hair by the candidate hair-coloring composition; ii. a predicted color-retention of the user hair following post-treatment washing(s) of the user's hair after coloring by the candidate hair-coloring composition; c. scoring each candidate hair-coloring composition according to competing scoring criteria such that: (i) a score of a candidate increases (decreases) as a candidate-specific predicted color-deviation between the target color state and the candidate-specific immediate-post-treatment color state decreases (increases); and (ii) a score of the hair-coloring composition increases (decreases) as the predicted color-retention improves, wherein the predicted color-retention is computed according to a plurality of colorant concentration-decay curves, one for each artificial colorant.

In some embodiments, the concentration-decay curves are damage-dependent to depend upon a predicted post-treatment damage-state of the user's hair.

In some embodiments, the auxiliary hair-state data includes a pre-treatment damage-state of the hair.

In some embodiments, the auxiliary hair-state data includes a thickness of the hair.

Some embodiments relate to a system for preparing a customized hair-coloring composition by dispensing material, the system comprising: a. computer storage for storing (i) a target color state and (ii) initial hair-state data describing at least an initial color-state of the user's hair; b. a computation-engine configured to compute, from the initial hair-state data and from the target color-state, a customized hair-coloring composition predicted to transform a color state of the user's hair from the initial color state towards (e.g. approximately to or exactly to) the target color state; and c. a user interface for receiving multi-objective relative-importance data describing a relative importance of first and second auxiliary objectives and optionally reaching the target color-state wherein: i. in response to receipt of multi-objective relative-importance data that prioritizes the first auxiliary objective the expense of the second auxiliary objective, the computation engine computes a hair-coloring composition that is predicted to better achieve the first auxiliary objective at the expense of the second auxiliary objective; and ii. in response to receipt of multi-objective relative-importance data that prioritizes the second auxiliary objective the expense of the first auxiliary objective, the computation engine computes a hair-coloring composition that is predicted to better achieve the second auxiliary objective at the expense of the first auxiliary objective.

Some embodiments relate to system for preparing a customized hair-coloring composition by dispensing material, the system comprising: a. computer storage for storing (i) a target color state and (ii) initial hair-state data describing at least an initial color-state of the user's hair; b. in response to receipt of multi-objective relative-importance data that prioritizes the first auxiliary objective the expense of the second auxiliary objective, the computation engine computes a hair-coloring composition that better achieves the first auxiliary objective at the expense of the second auxiliary objective; and c. a dispenser device having a plurality of containers, a different material being respectively disposed in each container, the dispenser device configured to respectively dispense a different quantity of material from each container in response to and according to computations performed by a digital computer; wherein: i. in response to receipt of multi-objective relative-importance data that prioritizes the first auxiliary objective the expense of the second auxiliary objective, the dispenser device dispenses materials from the containers at relative quantities for a hair-coloring composition that is predicted to better achieve the first auxiliary objective at the expense of the second auxiliary objective; and ii. in response to receipt of multi-objective relative-importance data that prioritizes the second auxiliary objective the expense of the first auxiliary objective, the dispenser device dispenses materials from the containers at relative quantities for a hair-coloring composition that is predicted to better achieve the second auxiliary objective at the expense of the first auxiliary objective.

In some embodiments, a first of the auxiliary objectives is last and a second of the auxiliary objective is gentleness.

In some embodiments, a first of the auxiliary objectives is uniformity/coverage and a second of the auxiliary objective is gentleness.

In some embodiments, a first of the auxiliary objectives is last and a second of the auxiliary objective is uniformity/coverage.

In some embodiments, a first of the auxiliary objectives is any first objective described herein and a second of the auxiliary objective is any second objective described herein.

BRIEF DESCRIPTION OF THE DRAWINGS

FIGS. 4, 5A-5C, 6A-6C, 7A-7B, 8A-8C, 9A-9F, 10A-10C, 11, 12A-12B, 13A-13B, 14A-14B and 15 relate to presently-disclose hair-coloring methods and systems

DETAILED DESCRIPTION OF EMBODIMENTS

The claims below will be better understood by referring to the present detailed description of example embodiments with reference to the figures. The description, embodiments and figures are not to be taken as limiting the scope of the claims. It should be understood that not every feature of the presently disclosed methods and apparatuses is necessary in every implementation. It should also be understood that throughout this disclosure, where a process or method is shown or described, the steps of the method may be performed in any order or simultaneously, unless it is clear from the context that one step depends on another being performed first. As used throughout this application, the word "may" is used in a permissive sense (i.e., meaning "having the potential to'), rather than the mandatory sense (i.e. meaning "must").

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Figure 4A:
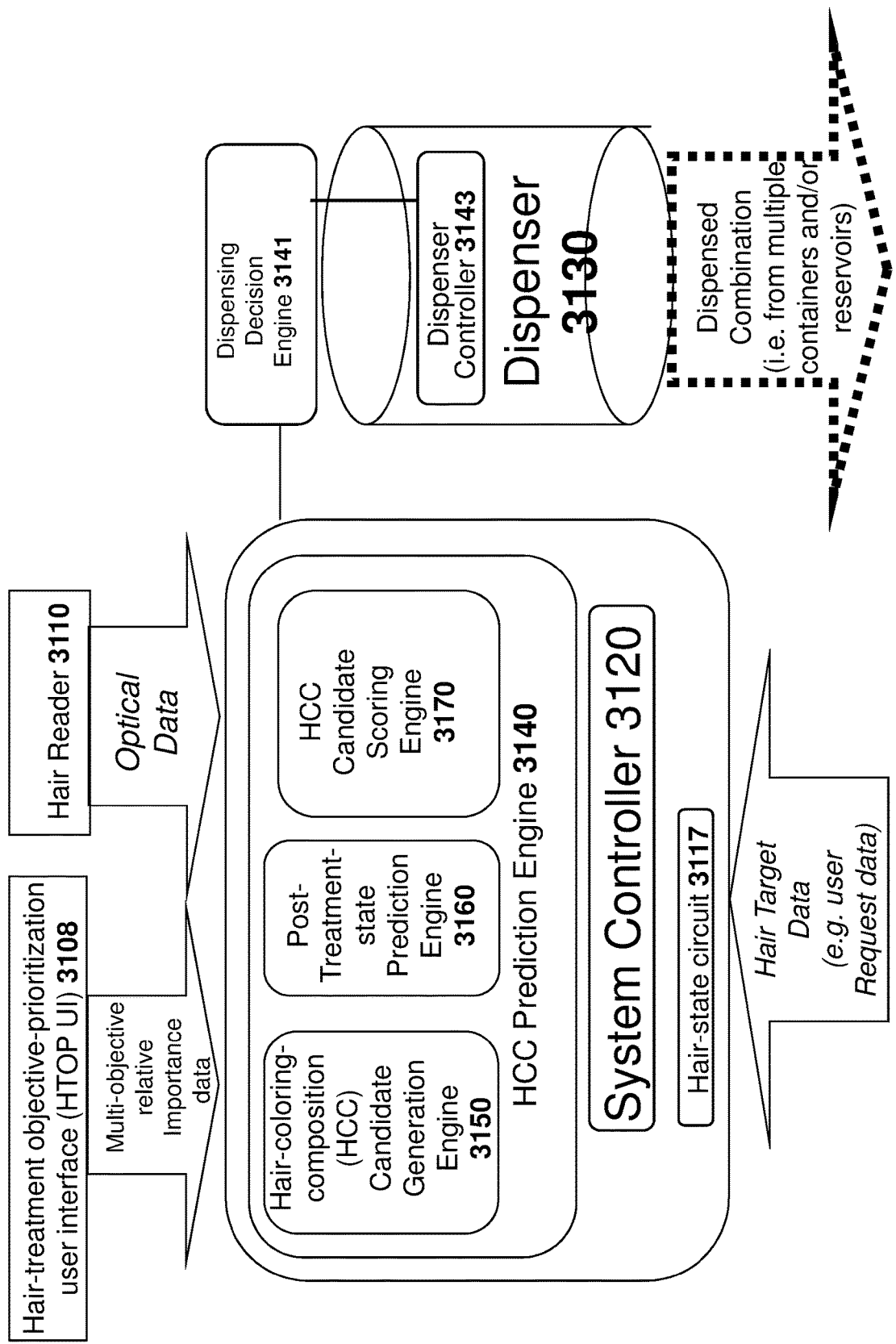
Figure 4B:
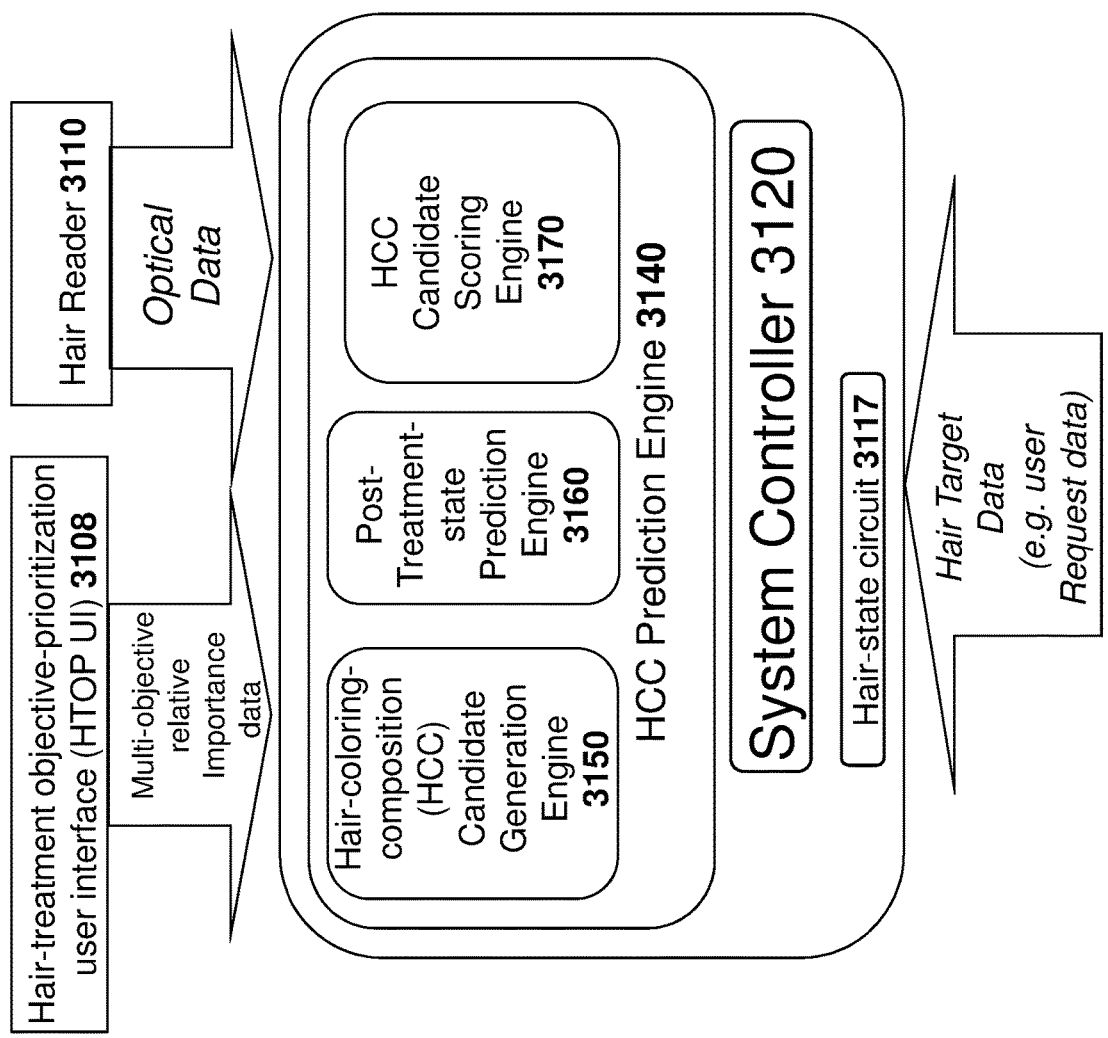

Embodiments of the present invention relate to hair-coloring systems include a hair-treatment objective-prioritization user interface (HTOP UI) 3108, and operates according to user-input received via the HTOP UI 3108. As will be discussed below in greater detail, the HTOP UI 3108 allows a user to explicitly specify the relative importance of various hair-coloring objectives including auxiliary objective(s), thereby prioritizing certain hair-coloring objectives over others. FIGS. 4A-4B, discussed below, are block diagrams of an example hair-coloring system including the HTOP UI 3108.

The primary objective remains the obtaining a HCC predicted to transform an immediate post-treatment color state of hair to a target (e.g. user-specified) color-state.

Thus, the hair-coloring systems computes a hair-coloring composition (HCC) predicted to transform a color-state of initial hair to a post-treatment color-state that, on some level, resembles a (e.g. user-specified) target color-state. The degree of accuracy (i.e. how close the predicted post-treatment color-state is to the target-state) may depend upon the user-specified data received via the HTOP UI 3108.

In particular, HTOP UI 3108 allows the user to specify how much of the immediate post-treatment color accuracy is to be sacrificed in order to achieve a competing hair-coloring goal, referred to as an 'auxiliary objective. Examples of auxiliary objectives include:

A. 'color last' or post-treatment color-retaining wash-robustness—i.e. when post-treatment washings have a minimal impact upon the color-state of post-treatment hair this impact a 'greater color last' than when post-treatment washings have a greater impact upon the color-state of post-treatment hair (see the discussion below with reference to FIGS. 8A-8C);

B. damage/gentleness—some hair-coloring treatments can inflict greater damage upon hair than others—e.g. hair-coloring treatments involving higher concentrations of oxidizing agents such as hydrogen peroxide inflict greater damage (see the discussion below with reference to FIGS. 13A-13B and 14A-14C;

C. coverage/uniformity—this may relate, for example, to natural gray hair (see the discussion below with reference to FIGS. 9A-9E).

Once the computerized hair-coloring system receives (i) a description of a color-state of the initial hair (i.e. pre-coloring-treatment), (ii) a description of the target coloring state (i.e. desired post-coloring-treatment state); and (iii) relative importance data specifying relative importance of one or more hair-treatment objectives (i.e. received via HTOP UI 3108), a hair-coloring composition (HCC) is computed. The computed HCC is predicted to transform the color state of 'initial hair' to the target color-state (i.e. not necessarily exactly to the target color-state—the degree of accuracy may be a function of what is achievable and may also depend upon the priority of immediate post-treatment accuracy) and is predicted to achieve the auxiliary objectives (i.e. not necessarily exactly—the degree of accuracy may be a function of what is achievable and may also depend upon the user-specified priority of each auxiliary objective specified via HTOP US 3108).

In some embodiments, the system dispenses (e.g. automatically) material (e.g hair-dying tablets for oxidative hair-coloring) for manufacturing the predicted HCC in response to computing of the HCC. The relative quantities of the different ingredients are determined by the computed HCC.

Figure 1:
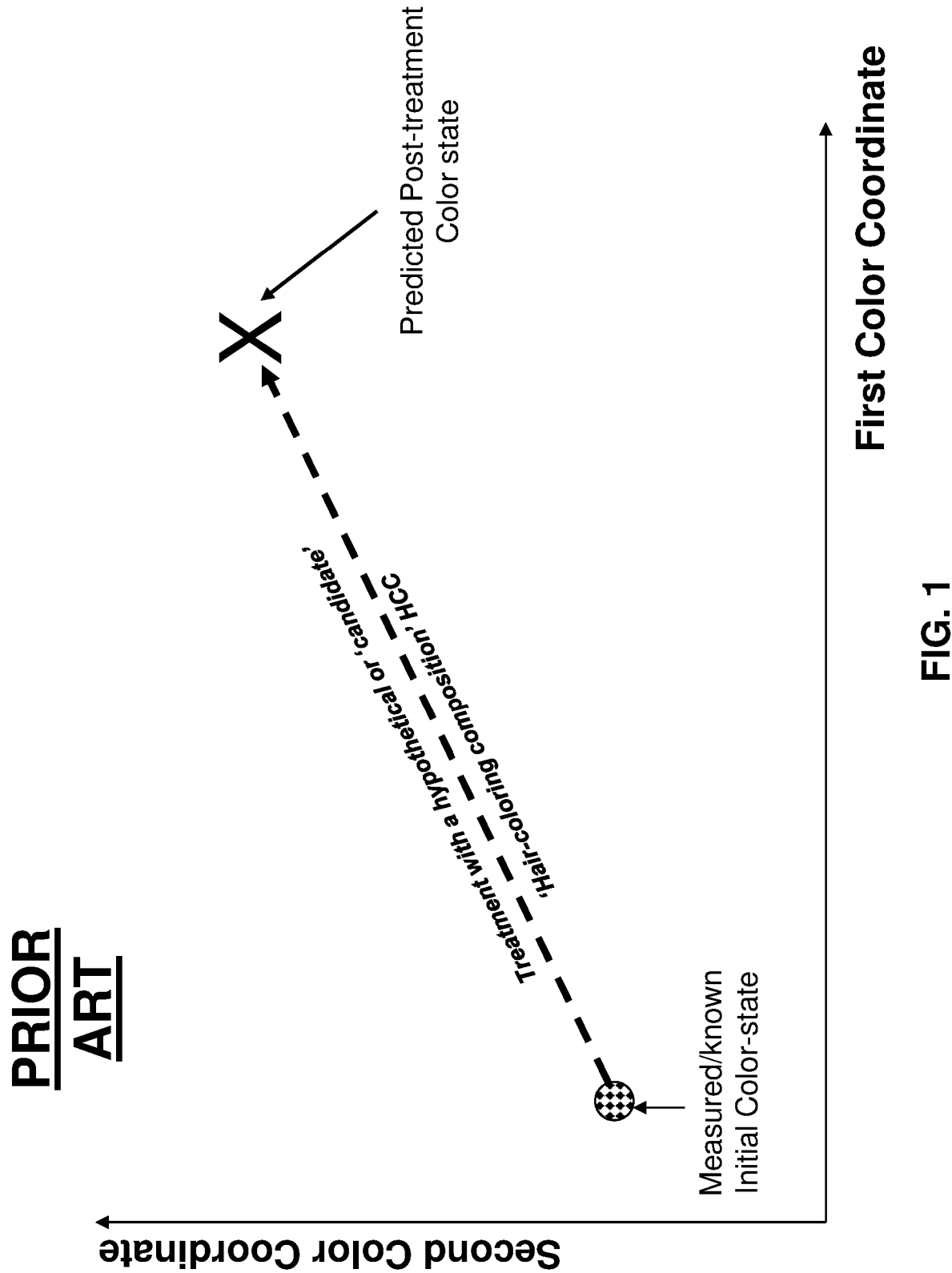
FIGS. 1, 2A-2B and 3 describe prior art techniques for hair-coloring.
Figure 2A:
Figure 2B:
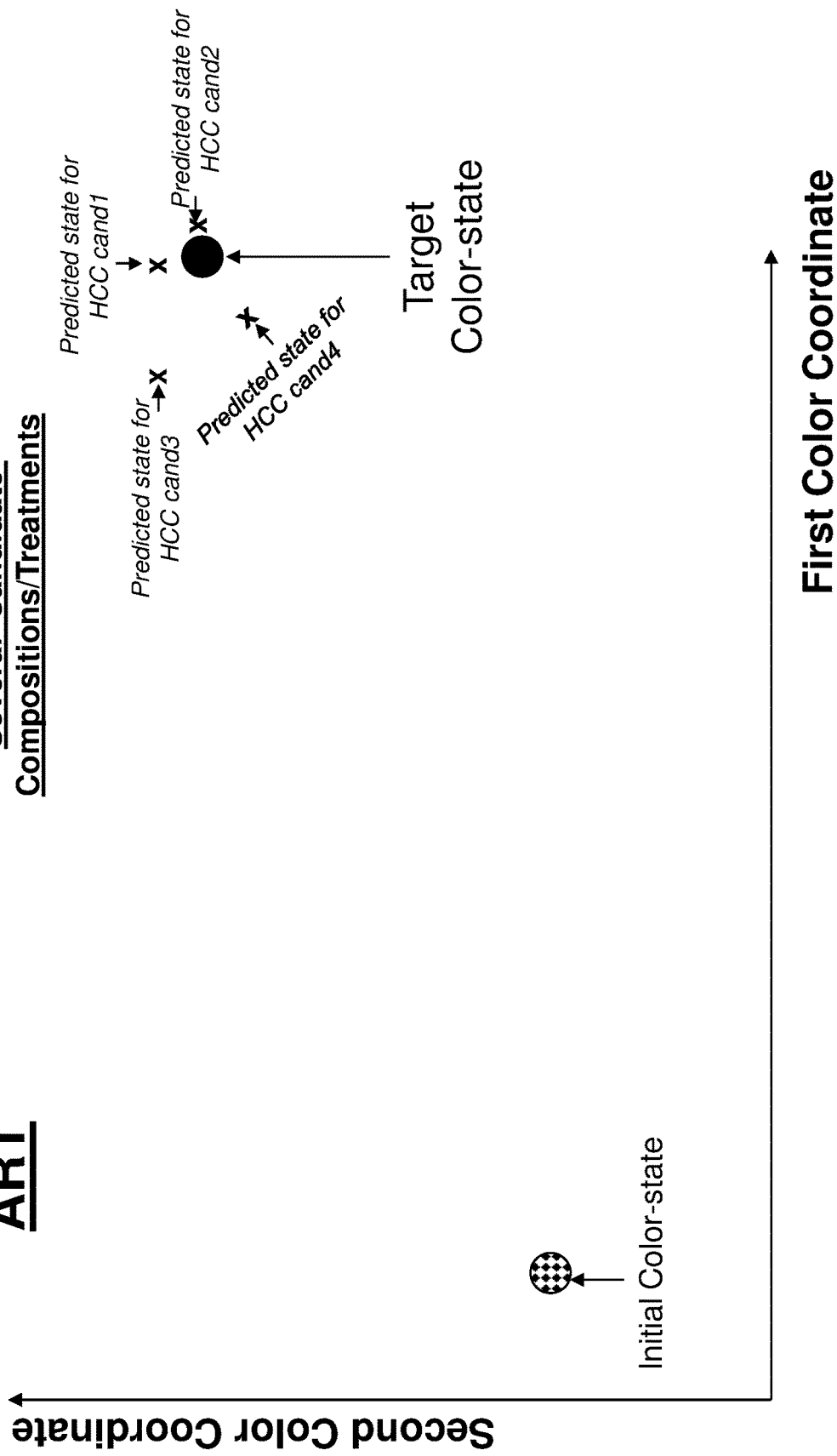
Figure 3:
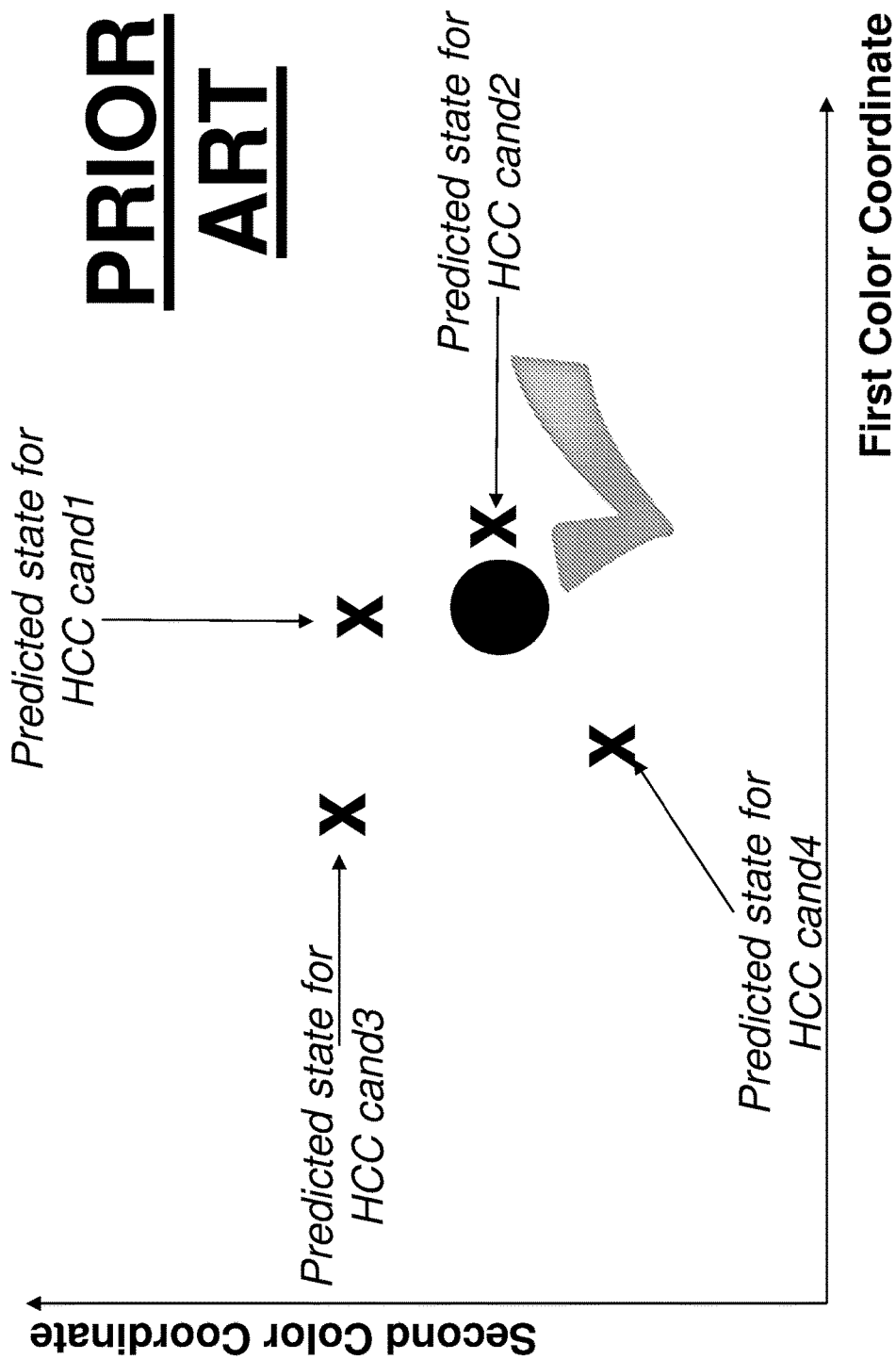

Instead of relying only on a 'hardwired' merit/scoring function (i.e. for scoring candidate HCCs) when computing a customized (e.g. optimal) coloring composition or dispensing ingredients for this composition (i.e. from different containers), embodiments of the present invention provide a user interface which allows a user to specify relative importance of competing and/or 'at least partially' contradicting hair-coloring goal. This allows for a greater degree of customization than possible in systems (e.g. see FIG. 3) where the merit/scoring function is hard-wired to be greedy with respect to immediate-post-treatment color-state. This also allows for a greater degree of customization than possible in systems where one or more auxiliary goals are taken into consideration when computing the HCC, but without user specification of their relative importance.

The prior art discussed in FIGS. 1, 2A-2B and 3 focuses on computing the HCC predicted to achieve the best possible (i.e. closest to the target-state (e.g. user-specified target-state)) post-treatment 'color-state.' In contrast, systems including the presently-disclosed HTOP UI 3108 allow for (i) computing (or dispensing ingredients) HCCs that sacrifice some accuracy in the immediate post-treatment color-state in order to achieve one or more of the 'auxiliary objectives' and (ii) allow for user-customization of relative importance of one or more of the auxiliary objectives relative to the importance of accuracy in the immediate post-treatment color-state (or the relative importance of one of the auxiliary objectives relative to another of the auxiliary objectives).

Figure 5A:
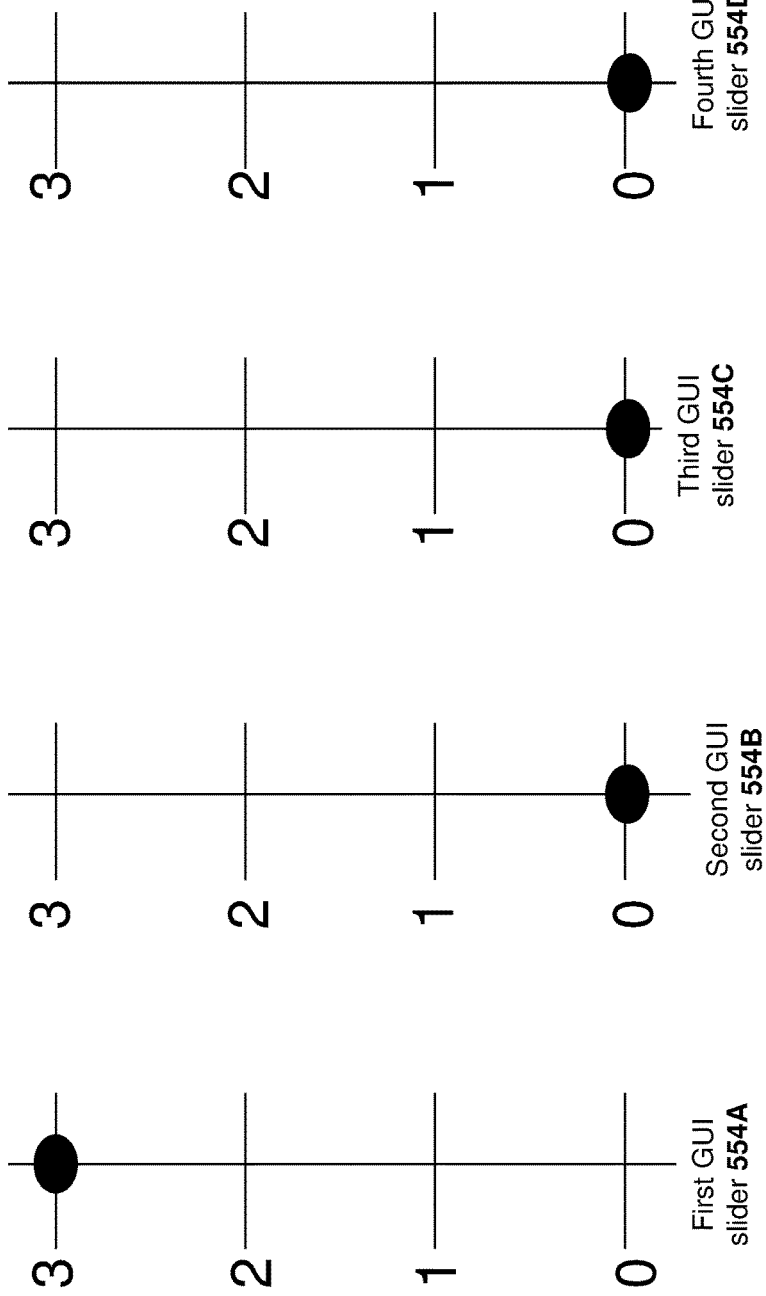
Figure 5B:
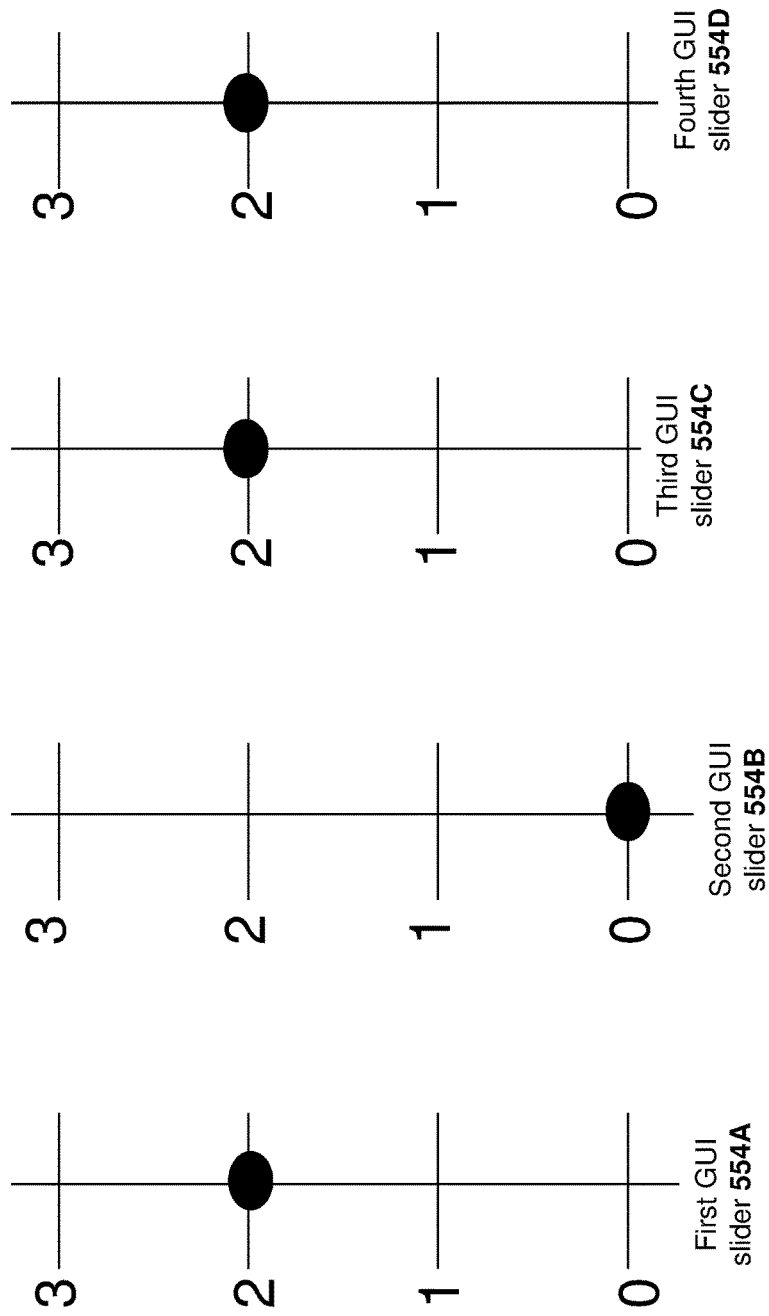
Figure 5C:
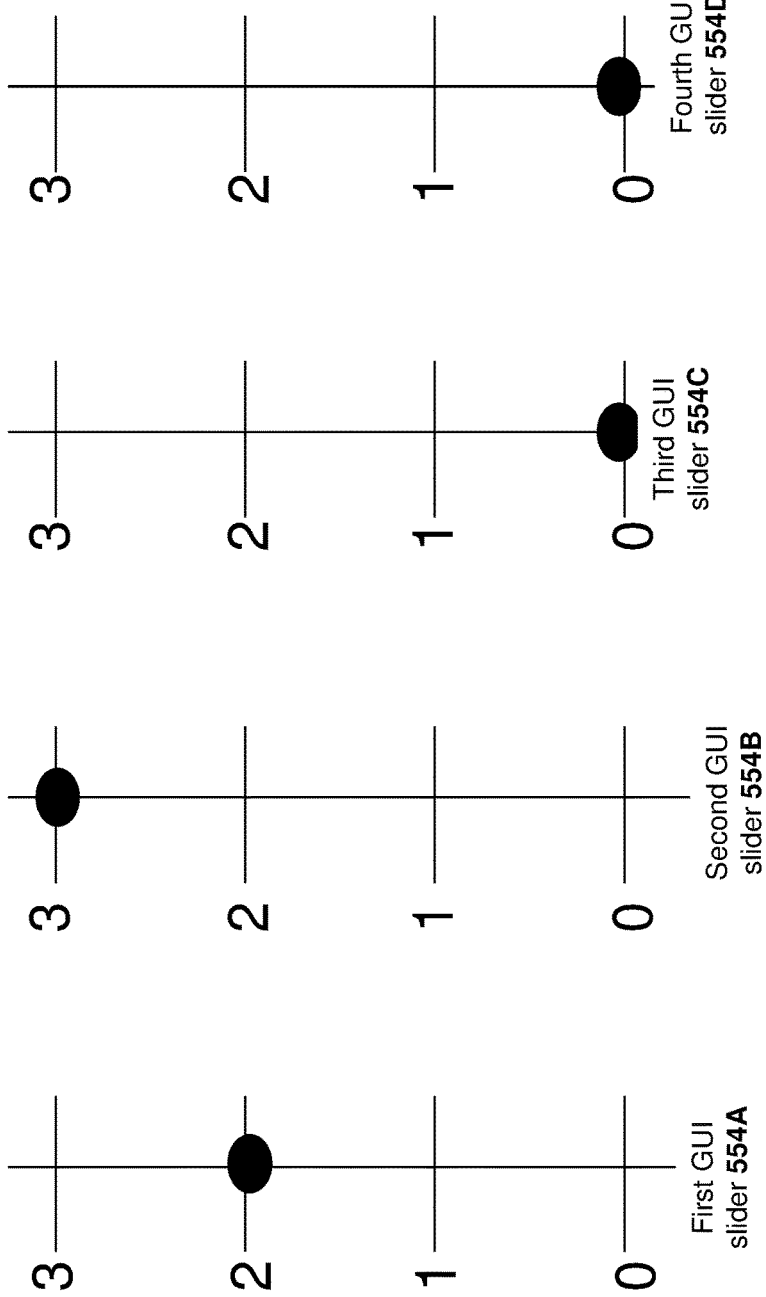
Figure 6A:
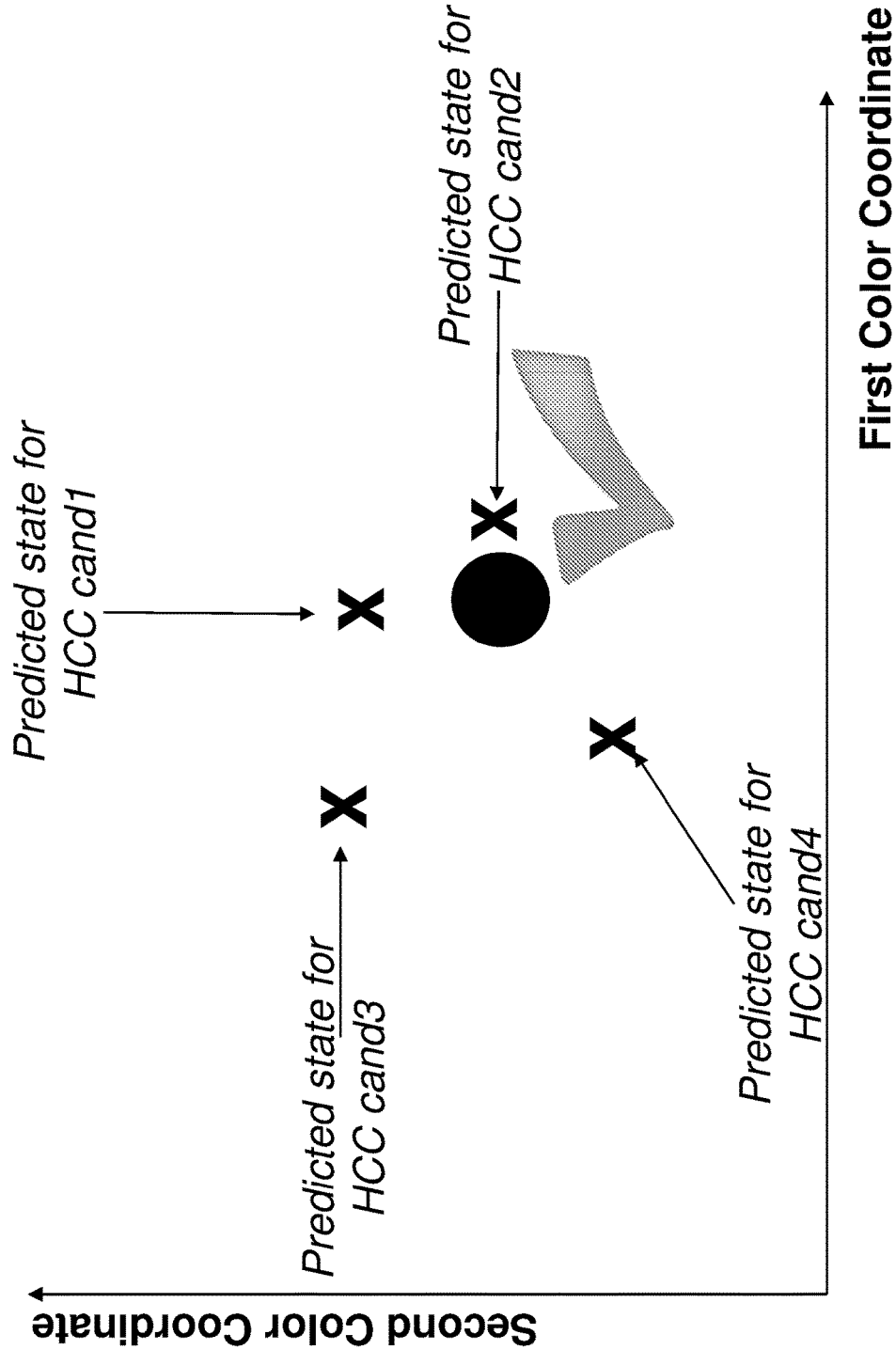
Figure 6B:
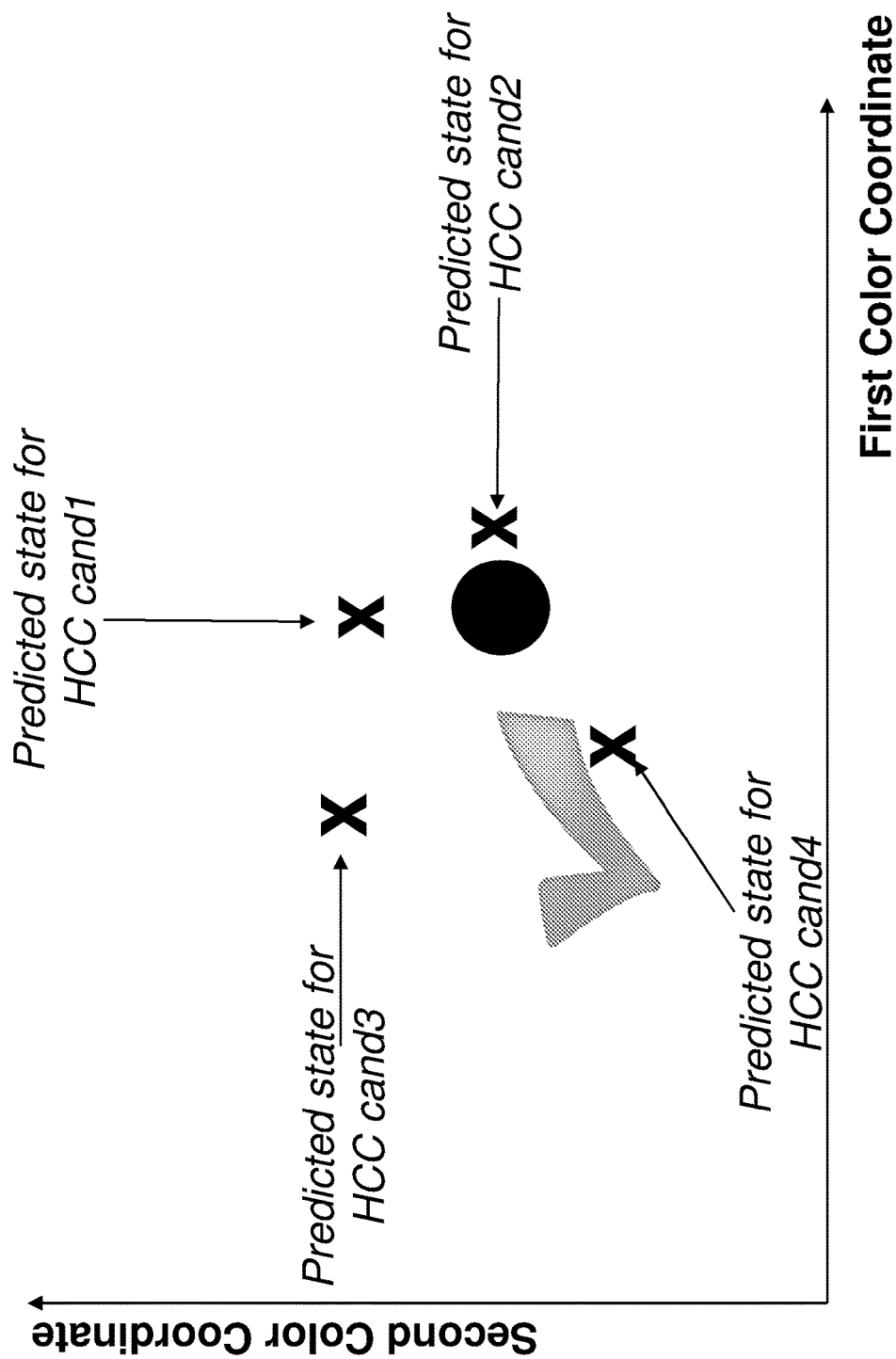
Figure 6C:
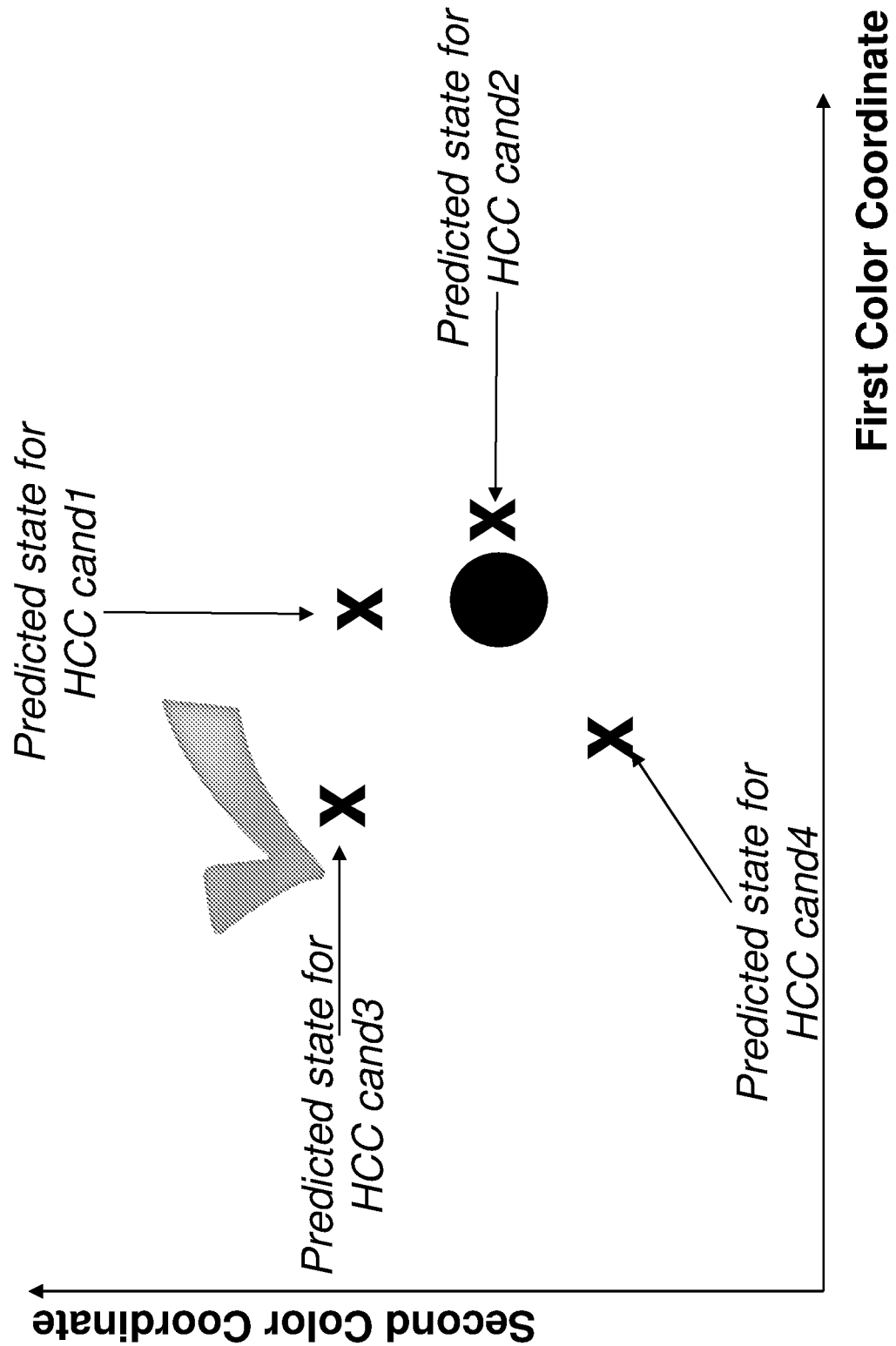

One example of an HTOP UI 3108 where a user can specify relative importance of immediate post-coloring accuracy is illustrated in FIGS. 5A-5C. Furthermore, a specific use-case related to this HTOP UI 3108 is presented, with reference to FIGS. 6A-6C. In the examples of FIGS. 6A-6C the initial pre-treatment hair-color state and the target post-treatment hair-color state is always the same.

In the example of FIGS. 5A-5B, HTOP UI 3108 comprises four GUI sliders 554A-554D. Each slider may be adjusted by the user to modify the overall scoring/merit function used to compute a customized hair-coloring composition and/or to dispense ingredients from containers of a dispenser at relative quantities to each other to achieve the customized hair-coloring composition.

The first GUI slider 554A corresponds to predicted immediate post-treatment accuracy, abbreviated as coloring accuracy. The other sliders 554B-554D, discussed below, correspond to auxiliary objectives, where slider 555B corresponds to 'last' (a feature discussed below—i.e. predicted 'last'), slider 555C corresponds to 'gentleness' or lack of damage (discussed below—i.e. predicted gentleness), and slider 554D corresponds to post-treatment color-uniformity (i.e. predicted post-treatment color-uniformity).

In the configuration of FIG. 5A (configuration A), the importance of immediate post-treatment accuracy is maximum, and the importance of all of the auxiliary objective is zero. In this case, candidate HCCs are be scored/ranked against each other according to the 'greedy' system described in FIG. 3 and any auxiliary goals are ignored. Thus, the only consideration is immediate post-treatment accuracy. This also corresponds to the situation of FIG. 6A where the selected HCC is HCC cand2, whose predicted post-treatment color-state is closest to the target.

In the configuration of FIG. 5A (configuration A), the importance of immediate post-treatment accuracy is maximum, and the importance of all of the auxiliary objective is zero. In this case, candidate HCCs are be scored/ranked against each other according to the 'greedy' system described in FIG. 3. Thus, the only consideration is immediate post-treatment accuracy. This also corresponds to the situation of FIG. 6A where the selected HCC is HCC cand2, whose predicted post-treatment color-state is closest to the target.

In contrast, in the configurations of FIG. 5B (configuration B) and FIG. 5C (configuration C), a certain degree of predicted immediate post-treatment accuracy is sacrificed for auxiliary goal(s). In the example of FIG. 5B, a certain degree of predicted immediate post-treatment accuracy is sacrificed for the sake of a combination of gentleness and uniformity—thus, in corresponding FIG. 6B, HCC cand4 is selected, even though the post-treatment predicted color state of HCC cand2 is better (i.e. more closely resembles the target color-state). This is because other considerations (i.e. as prioritized by GUI 3108 in FIG. 5B) cause HCC cand4 to score better, due to better predicted gentleness and/or better predicted uniformity. Thus, HCC cand4 would be predicted to provide a more gentle treatment and/or better uniformity than HCC cand2.

In the example of FIG. 5C, a certain degree of predicted immediate post-treatment accuracy is sacrificed for the sake of 'last'—thus, in corresponding FIG. 6C, HCC cand3 is selected, even though the post-treatment predicted color state of HCC cand2 is better (i.e. more closely resembles the target color-state). This is because other considerations (i.e. as prioritized by GUI 3108 in FIG. 5B) cause HCC cand3 to score better, due to better predicted last. The immediate post-treatment color of HCC cand2 is predicted to more closely resemble target—however, HCC cand3 is selected because it is predicted to provide better last—i.e. to retain a color closer to the target color even after washings.

In some embodiments, when computing a score (see step S117 discussed below) of a candidate HCC, it is possible to compute a composite score, which takes into account immediate post-coloring-treatment color accuracy and one or more auxiliary objective(s). One non-limiting example of a composite score $Score_{COMPOSITE}$ ( ) is a weighted average, as shown in Eqn. 1:

$$Score_{COMPOSITE} = \frac{\sum_{i=1}^{num\_of\_scores} \alpha_i Score_i}{\sum_{i=1}^{num\_of\_scores} \alpha_i} \quad \text{(Eqn. 1)}$$

where $Score_i$ (i=1) is a score based exclusively on post-coloring-treatment color accuracy, or (when i>1) exclusively on a single auxiliary objective. num_of_scores is the number of scoring categories, and $\alpha_i$ are the weighing coefficients.

In the example of FIGS. 5A-5C and 6A-6C, there are four scoring categories (num_of_scores=4) as follows:

(i) i=1; $Score_1$ is a score based exclusively on predicted post-coloring-treatment color accuracy, like in FIG. 3 the closer the predicted color-state resembles the target (e.g. smaller deviations in color space), the greater $Score_1$;

(ii) i=2; $Score_2$ is a score based exclusively on predicted last—the longer the predicted hair-color state is predicted to retain its color (i.e. against washing), the greater $Score_2$. In order to compute $Score_2$, it may be necessary to predict 'last'—example techniques for predicting last are disclosed below, with reference to FIGS. 8A-8C.

(iii) i=3; $Score_3$ is a score based exclusively on predicted gentleness—the less damage a hair-coloring treatment is predicted to inflict upon the hair, the greater $Score_3$. In order to compute $Score_3$, it may be necessary to predict the 'damage'—example techniques for predicting the damage are disclosed below, with reference to FIGS. 13A-13B and 14A-14B.

(iv) i=4; $Score_4$ is a score based exclusively on predicted post-treatment hair-color uniformity—the more uniform the hair-color is predicted to be with respect to color, the greater $Score_4$. In order to compute $Score_4$, it may be necessary to predict the 'uniformity'—example techniques for predicting the damage are disclosed below, with reference to FIGS. 9A-9F.

In Eqn. 1, $\alpha_i$ are the weighing coefficients. In FIG. 5A, $\alpha_1=3$, $\alpha_2=0$, $\alpha_3=0$, and $\alpha_4=0$. In FIG. 5B, $\alpha_1=2$, $\alpha_2=0$, $\alpha_3=2$, and $\alpha_4=2$. In FIG. 5C, $\alpha_1=2$, $\alpha_2=3$, $\alpha_3=0$, and $\alpha_4=0$.

It is noted that the 'sliders' is just one particular example of receiving the data via a user interface—the skilled artisan will appreciate that way of receiving the data into the user interface known in the art may be used—e.g. radio buttons, text box, etc.

Another feature of FIGS. 5A-5D is that a plurality of pre-determined options are presented for immediate/—for each category, the user selects one option from the plurality of pre-determined options.

Also, in some embodiments, instead of (or in addition to) providing information about how to weigh and 'auxiliary goal' against the main 'color accuracy goal' in some embodiments the user interface (i.e. and the digital computer and/or engine and/or dispenser respond accordingly) allows the user to provide information to weigh a first auxiliary goal against a second auxiliary goal.

In non-limiting examples, any one of the of the following 'auxiliary goals' may be weighed against the 'color accuracy goal' or against another of the following auxiliary goals: (i) robustness/last; (ii) gentleness/minimizing damage/(iii) coverage/uniformity; (iv) treatment simplicity (i.e. to minimize the number of bowls and/or treatment steps required).

Figure 7A:
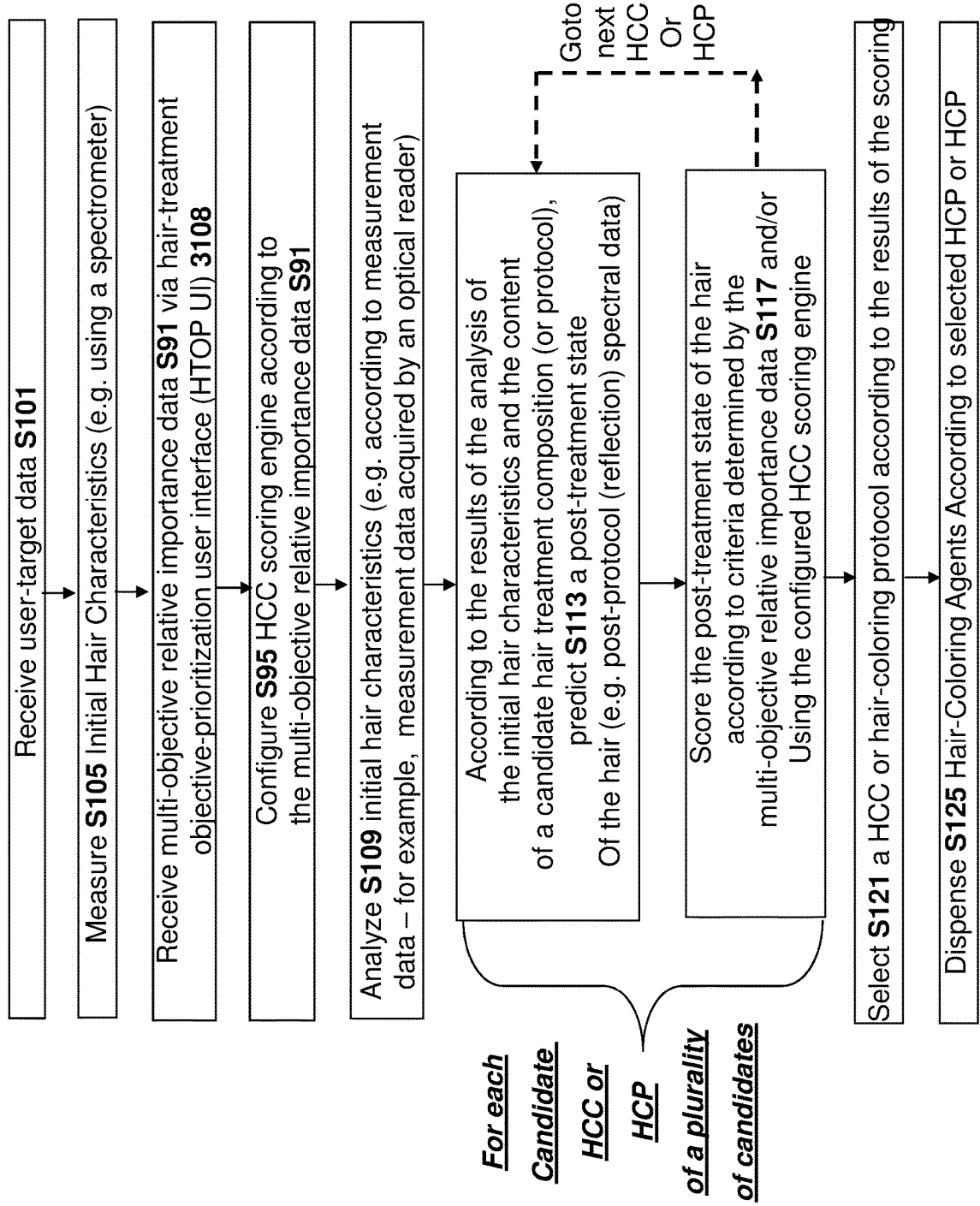
Figure 7B:
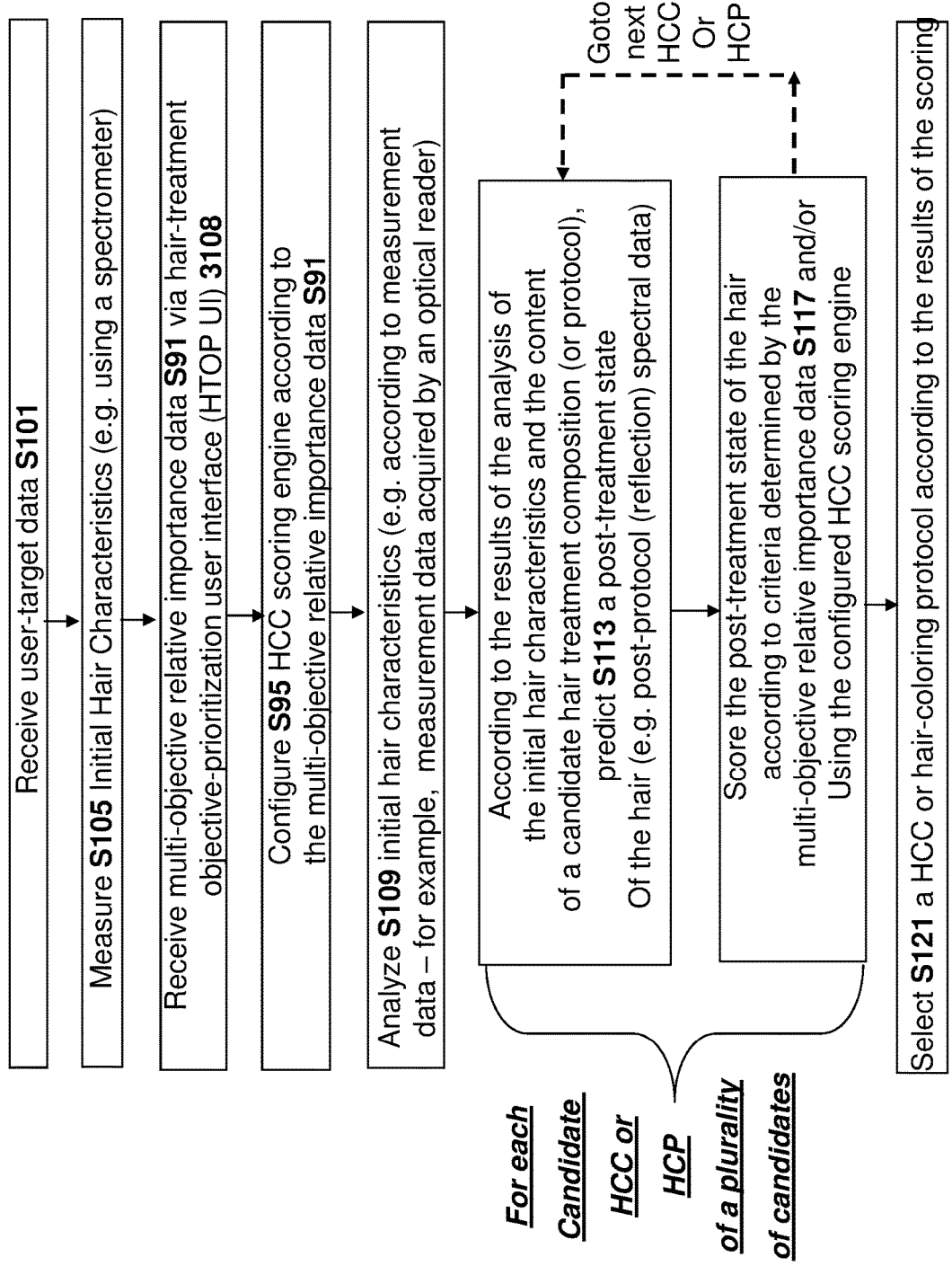

FIGS. 4A-4B. discussed below, illustrates one example of a system including the hair-treatment objective-prioritization user interface (HTOP UI) 3108. FIGS. 7A-7B are flow-charts of methods that may be performed using the system of FIG. 4A or FIG. 4B The system of FIGS. 4A-4B (i) allows the user to define, via GUI 3108, specific scoring criteria for auxiliary objectives by which potential HCC is evaluated; (ii) includes computational engines (discussed below) for analyzing initial-hair data (e.g. acquired via hair reader 3110) and for rating/scoring a potential HCC; and (iii) optionally includes and/or is operatively linked to a dispenser 3130 for dispensing a customized combination of materials from different containers dispenser 3130.

HTOP UI 3018 allows for specifying one or more 'auxiliary goals', defined as a goal other than immediate-post-treatment predicted similarity between a target color-state and a predicted immediate-post-treatment color-state.

As discussed above, the 'main' goal of coloring accuracy may 'compete with' and/or at least partially contradict with one or more auxiliary goals. Also, the auxiliary goals may 'compete with' and/or at least partially contradict each other—e.g a first auxiliary goal may compete with' and/or at least partially contradict a second auxiliary goal.

HCC prediction engine (e.g. responsive to input received via the HTOP UI 3108) is configured to compute, from the initial hair-state data and from the target color-state, a customized hair-coloring composition predicted to transform a color state of the user's hair from the initial color state to the target color state. HTOP UI 3018 allows for customizing operation of the HCC prediction engine to compute an HCC optimized according to use-specified weights for one of more auxiliary objectives. Thus, the user can specify (i) the relative importance of one or more auxiliary objectives relative to the standard objective of immediate post-treatment color accuracy and/or (ii) the relative important of a first auxiliary objective relative to a second auxiliary objective.

Instead of relying only on a 'hardwired' merit/scoring function when computing a customized (e.g. optimal) coloring composition or dispensing ingredients for this composition (i.e. from different containers), embodiments of the present invention provide a user interface which allows a user to specify relative importance of competing and/or 'at least partially' contradicting hair-coloring goal. This allows for a greater degree of customization than possible in systems where the merit/scoring function is hard-wired to be greedy with respect to immediate-post-treatment color-state (e.g. see FIG. 3). This also allows for a greater degree of customization than possible in systems where one or more auxiliary goals are taken into consideration when computing the HCC, but without user specification of their relative importance.

The system of FIGS. 4A-4B may include one or more of (i.e. any combination of) the following elements: HTOP UI 3108, HCC prediction engine 3140, hair-state circuit 3117, hair reader 3110, system controller 3120, dispensing decision engine 3141, and dispenser device 3130. In the non-limiting implementation of FIGS. 4A-4B, system controller 3120 includes and/or is linked to HCC prediction engine 3140.

As will be discussed below, in the non-limiting implementation of FIGS. 4A-4B, HCC prediction engine 3140 comprises:

(i) HCC candidate generation engine 3150 which generates data representing a potential or candidate HCC solution whose properties are considering (e.g. the data may describe relative quantities of different types of hair-coloring dyes, concentration of different artificial colorants, any other representation known to the skilled artisan after reading this disclosure)—typically HCC candidate generation engine 3150 generates data describing a plurality of candidates (e.g. at least thousands or at least millions) which are analyzed. HCC candidate generation engine 3150 may use techniques known in or related to combinatorics for generating candidate HCCs to be analyzed from myriad possibilities—e.g. a searching technique such as genetic algorithms may be employed;

(ii) post-treatment-state prediction engine 3160 which may compute a prediction of a post-hair-coloring treatment state (e.g. after treatment with one of the candidate HCC as generated by engine 3150) of the initial hair (e.g. having properties measured, for example, by reader 3110). In different embodiments, post-treatment-state prediction engine 3160 may compute a prediction of one or more properties related to an auxiliary objective—for example, a post-treatment damage state, or a post-treatment ability of the hair to retain its color against post-treatment washings, a post-treatment color uniformity, or any other properties;

(iii) HCC candidate scoring engine 3170—for example, the scoring engine 3170 may be configurable or customized by input received via HTOP UI 3108. Each candidate HCC associated with a respective predicted post-treatment state or properties (e.g. computed by engine 3160). In order to score or grade a candidate HCC, its predicted post-treatment state or properties may be scored or analyzed. Thus, for $Score_1$ of FIGS. 5A-5C, the score is based only upon the predicted deviation between the predicted immediate-post-treatment color-state and the target state. However, a composite score may be used—one non-limiting example is presented above with reference to Eqn. 1. In that example, the user specifies via HTOP UI 3108 that alpha coefficients, to configure operation of HCC candidate scoring engine 3170—in this manner, HTOP UI 3108 may configure operation of HCC prediction engine 3140. System controller 3120 and/or HCC prediction engine 3140 may output/select the HCC candidate having the greatest score, according to criteria used by and/or output of scoring engine 3170.

Also as illustrated in FIGS. 4A-4B, the system may comprises one or more of the following elements:

i. a hair-state circuit 3117 configured to store a target color state for the potential hair-coloring treatment and/or initial hair-state data describing at least an initial color-state of the user's hair before being subjected to the potential hair-coloring treatment—in some embodiments, the circuit 3117 may store one or more rules. In different embodiments, circuit 3117 comprises volatile and/or non-volatile computer-readable storage;

ii. Hair reader 3110 which optically acquires optical data from hair—for example by illuminating the hair and detecting light reflected by and/or transmitted by and/or deflected by the hair iii. System controller 3120 (e.g. comprising a digital computer) receives both the optical data and hair target data (e.g. describing a target shade desired the user;

iv. dispensing decision engine 3141 may decides and/or commands dispenser to dispense material from containers of dispenser 3130 at relative quantities of the HCC computed/output by HCC prediction engine 3140 (e.g. in response to). Electronic controller 3143, which controls operation of dispenser 3130 then executes the command and causes the materials to dispensed from containers of dispenser 3130;

The dispenser proceeds to dispense the materials (e.g. into a mixing vessel—NOT SHOWN) for the hair-coloring composition. These materials may be automatically or manually mixed to form a customized hair-coloring composition, which is applied to the user's hair.

In various examples, the hair-reader 3110 may be or include any one or more (i.e. any combination) of the following: a camera or any other imaging device, a spectrometer (e.g. including 'color-dispersion optics'), a spectrograph, a hyperspectral imaging device. In different examples, a reflection and/or absorption and/or transmission spectrum may be measured. Color-state data may be acquired by any of these instruments.

Also shown in FIGS. 4A-4B is user interface 3108 (e.g. graphical-user-interface (GUI)) which may include a display screen (e.g. of a computer-kiosk or of desktop computer or of a laptop or of a mobile phone of a tablet device—it may be a touch screen but is not required to be). The user interface 3108 presents (e.g. displays) information to a user and receives data from the user. In some embodiments, 'target color state' or 'hair-target data' is also received via a user interface (either 3108 or another user interface).

As shown in FIG. 4B, there is no requirement to include a hair reader 3110 (or any other device for measuring property(ies) of the hair). Alternatively or additionally, initial hair data describing pre-treatment property(ies) of hair may be provided in another manner—e.g. via GUI.

Figure 11:
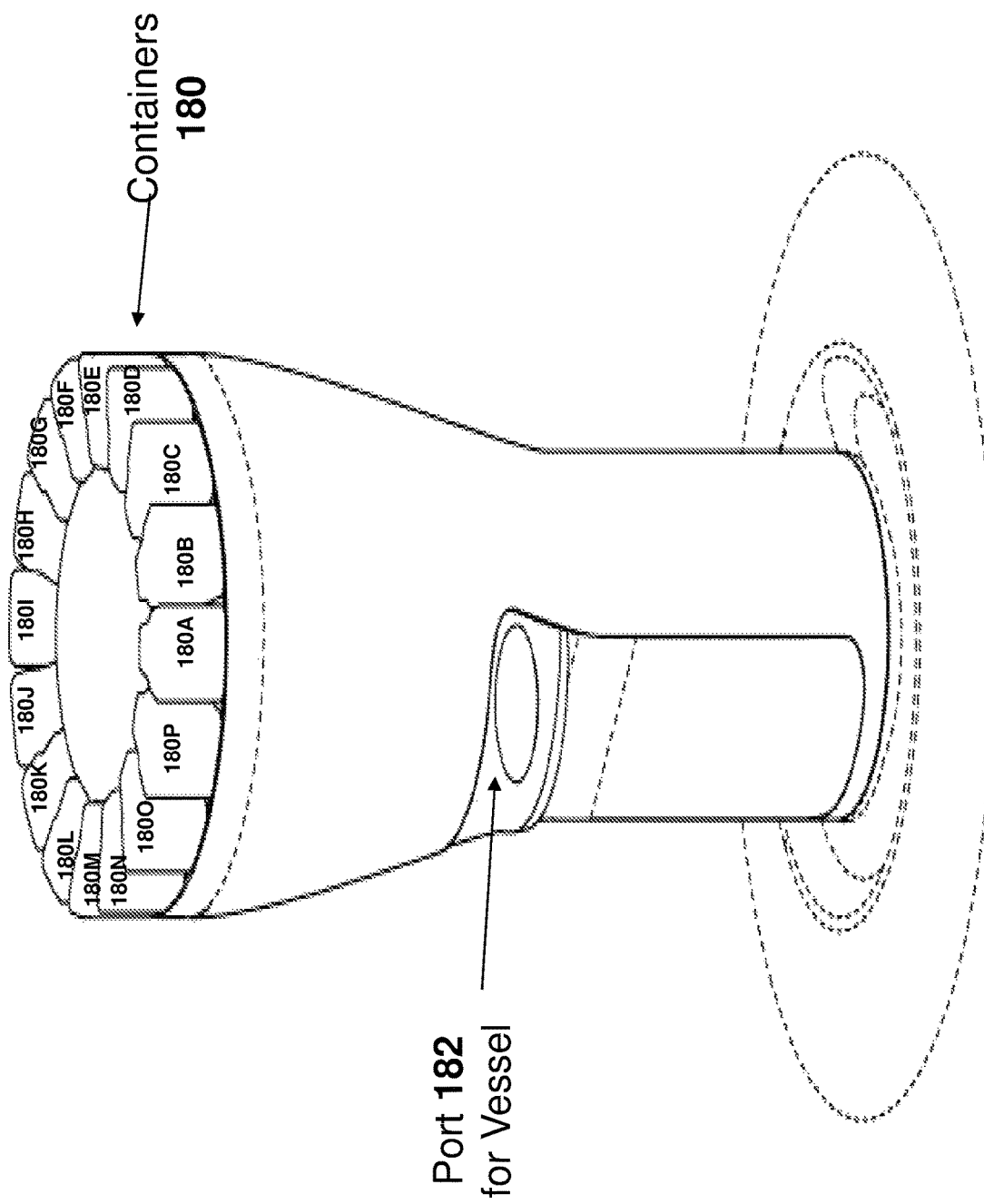

One non-limiting example of a dispenser 3130 of hair-coloring agents is illustrated in FIG. 11. In this non-limiting example, a plurality of containers 180A-180Q are engaged to dispenser 3130, such that each container contains therein different respective material related to hair-coloring. Dispenser 3130 dispenses a combination of these material into a mixing vessel (NOT SHOWN)—e.g. located in port 182.

In one example, one or more of 3140, 3150, 3141, 3143, 3160, 3117 and/or 3170 is implemented as software stored in volatile or non-volatile memory).

Electronic circuitry or any 'digital computer' or any kind of 'engine' may include may include any executable code module (i.e. stored on a computer-readable medium) and/or firmware and/or hardware element(s) including but not limited to field programmable logic array (FPLA) element(s), hard-wired logic element(s), field programmable gate array (FPGA) element(s), and application-specific integrated circuit (ASIC) element(s). Any instruction set architecture may be used including but not limited to reduced instruction set computer (RISC) architecture and/or complex instruction set computer (CISC) architecture. Electronic circuitry may be located in a single location or distributed among a plurality of locations where various circuitry elements may be in wired or wireless electronic communication with each other.

Figure 12A:
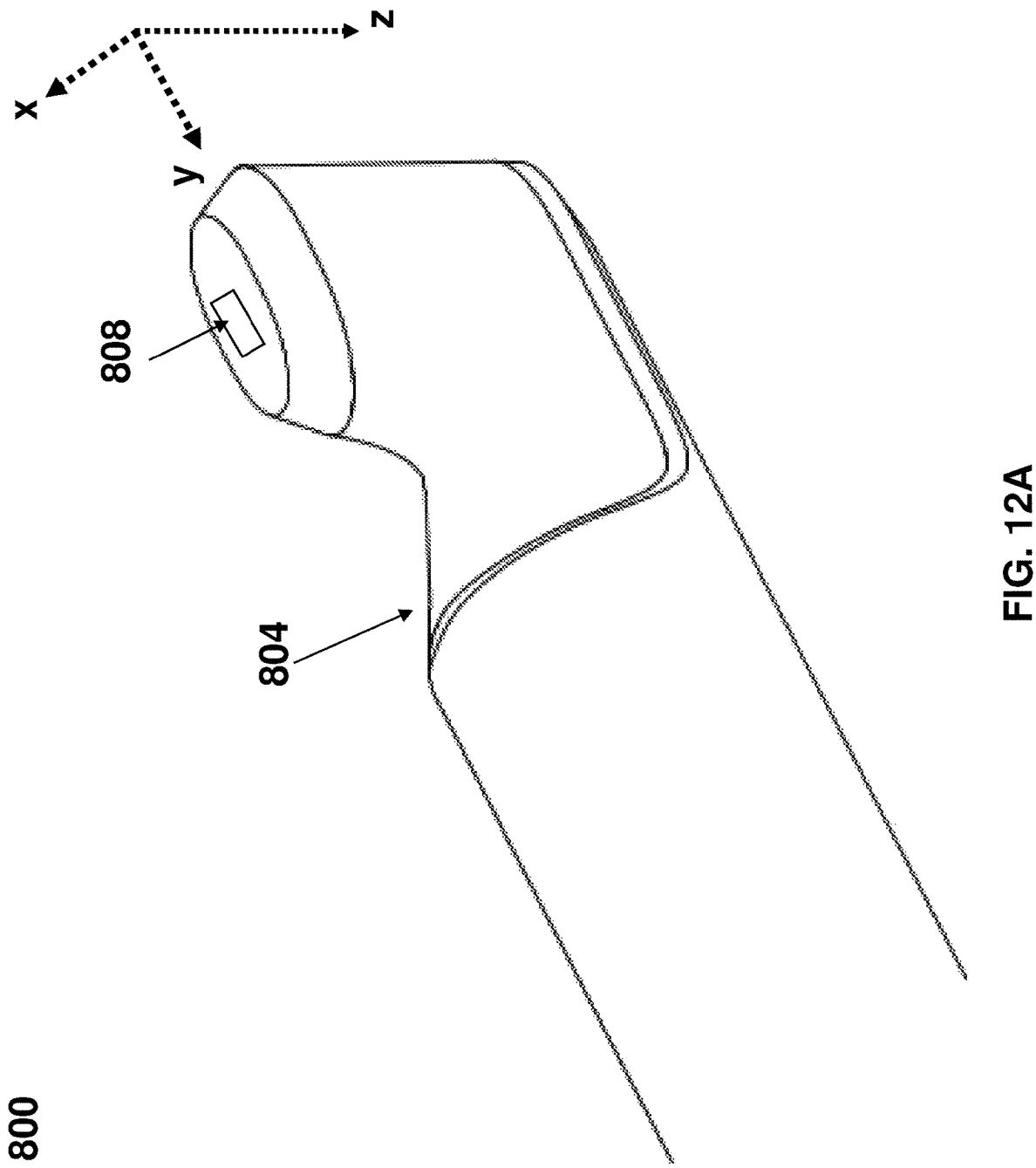
Figure 12B:
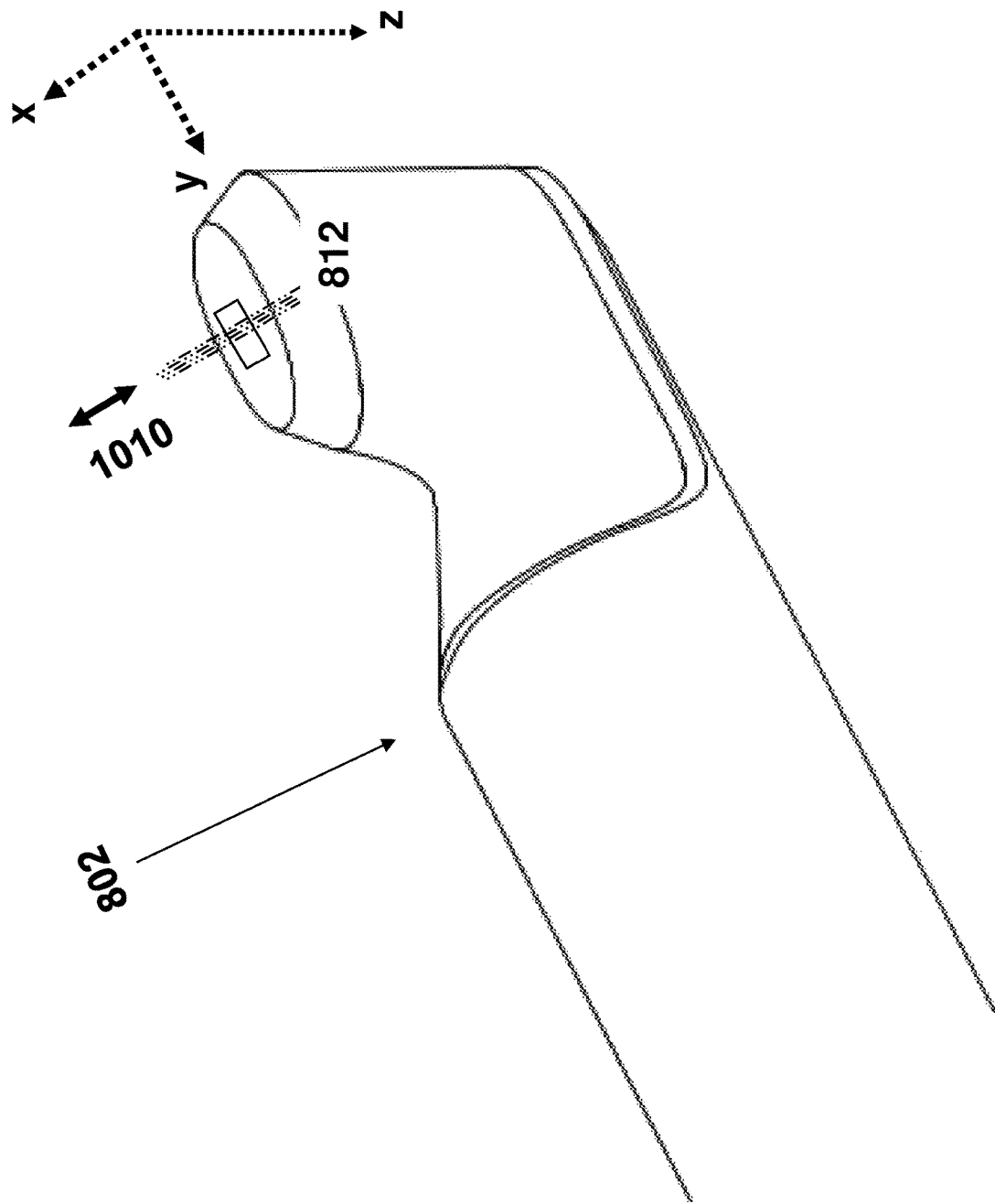
Figure 13A:
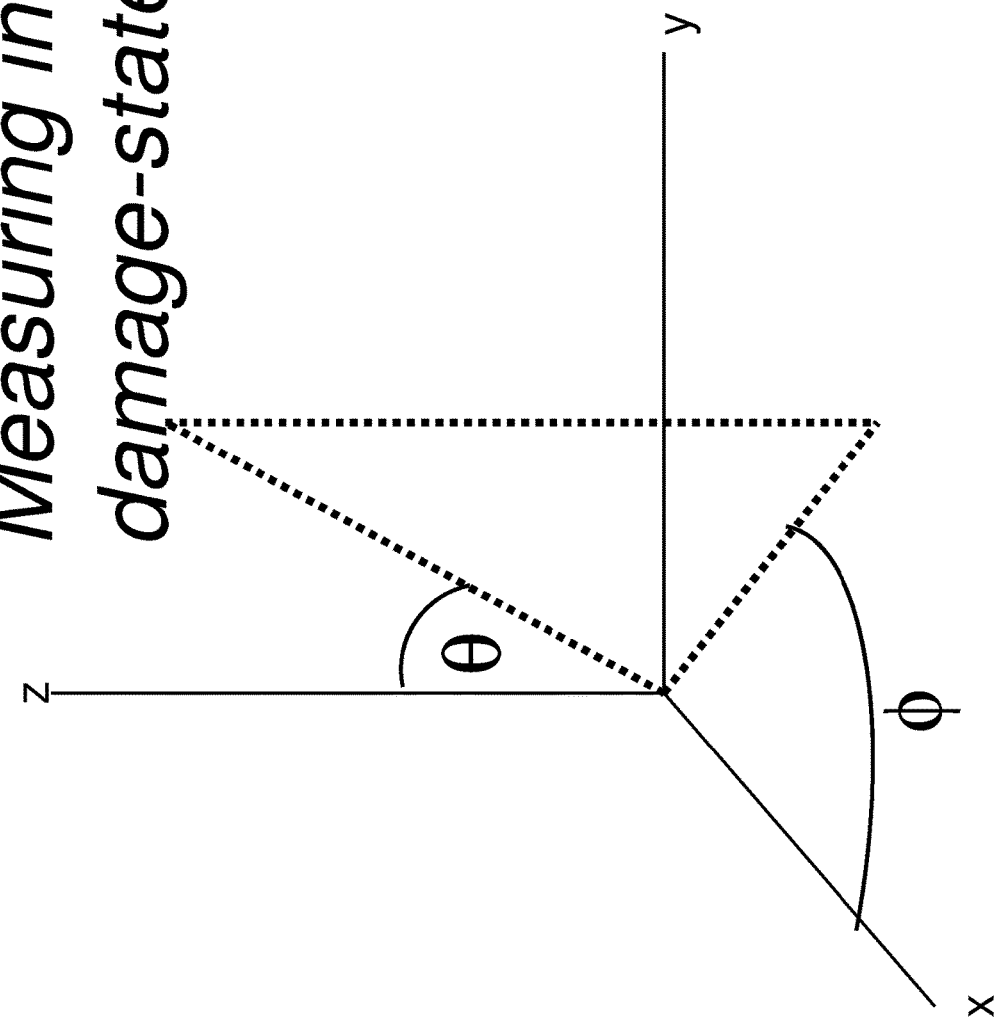
Figure 13B:
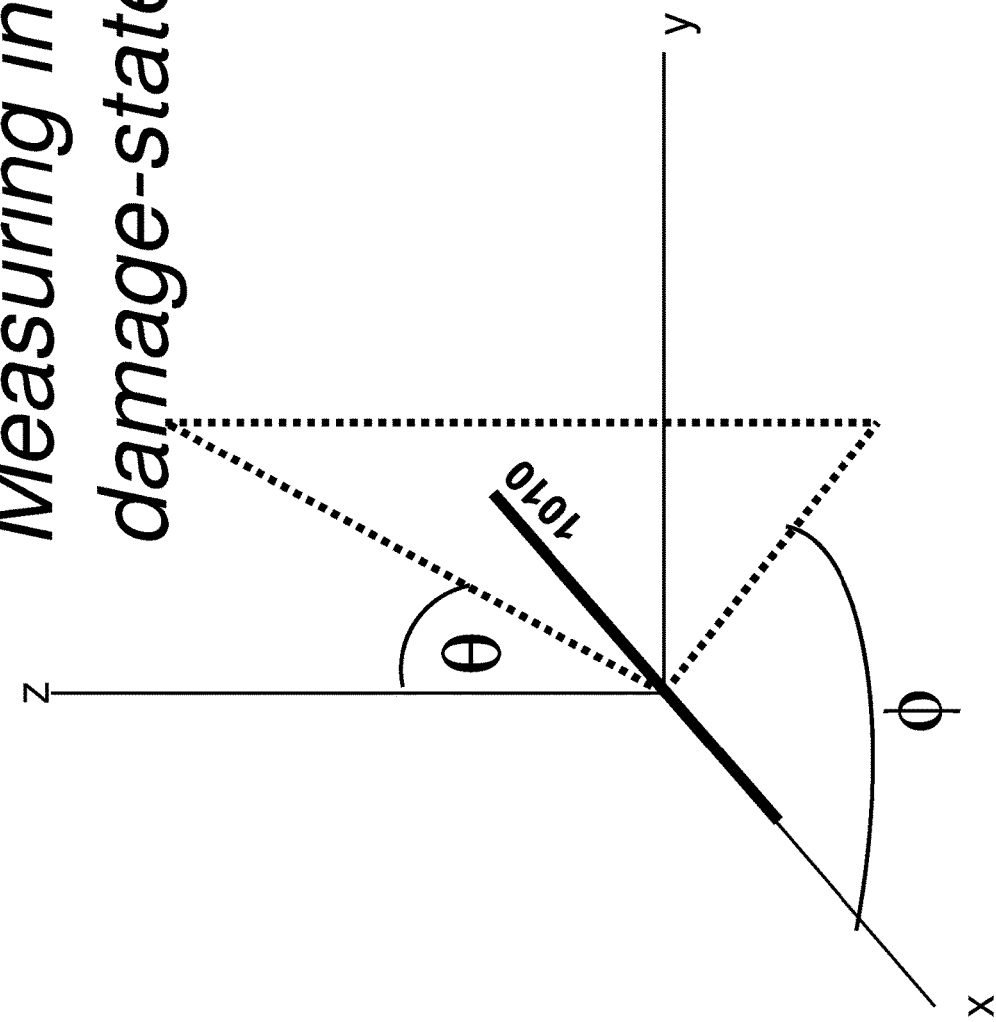
Figure 14B:
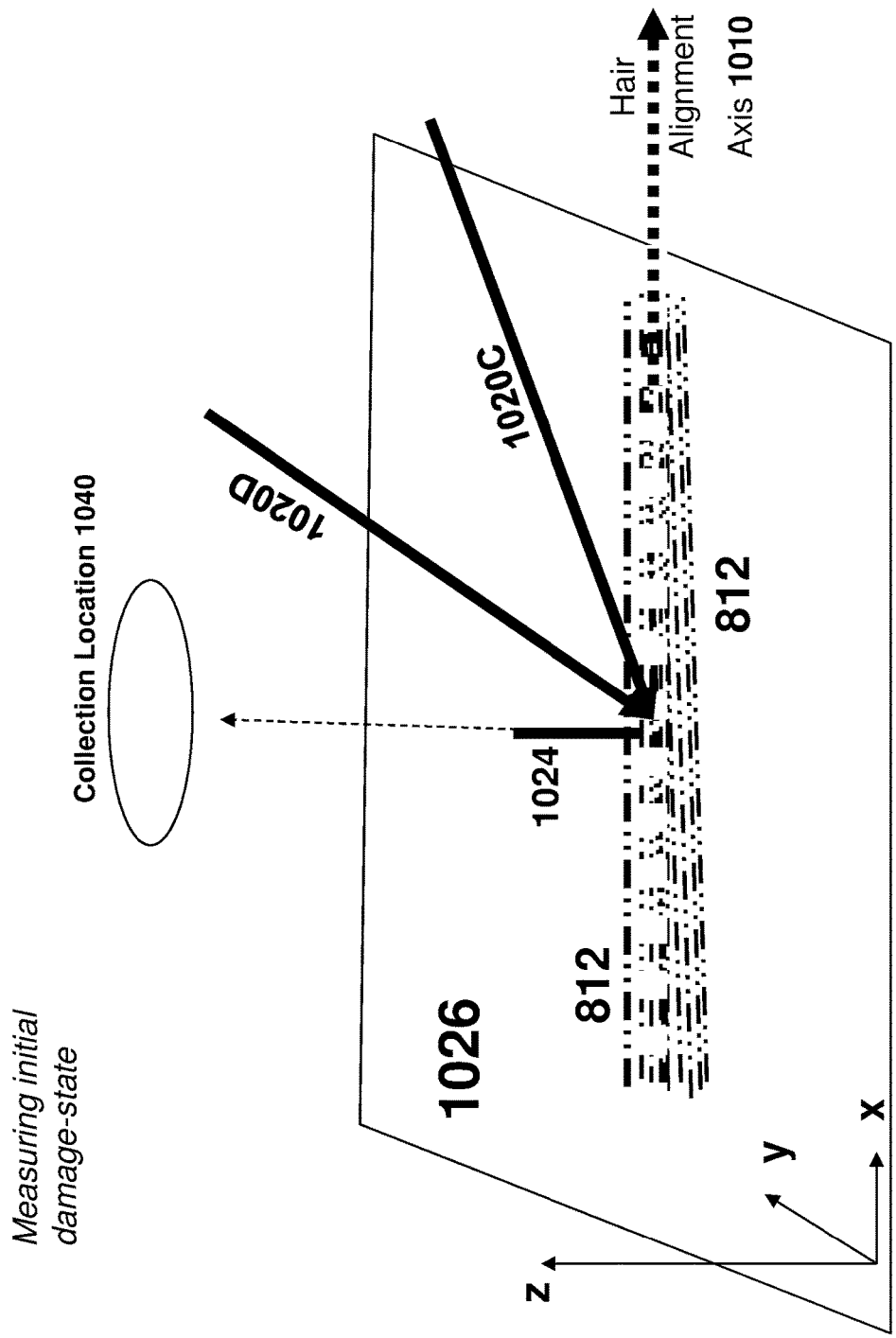

FIGS. 12A-12B illustrate a non-limiting example of a hair-reader 3110 in accordance with some embodiments. Hair-reader 3110 includes a housing 804 (e.g. opaque) and a window 808. In FIG. 12B, a plurality of keratinous fibers 812 are substantially aligned along an alignment axis which corresponds to the 'y' axis.

FIGS. 7A-7B is a flow-chart of a non-limiting example of a technique for hair-coloring for example, using the system of FIG. 4A or 4B. The skilled artisan will appreciate that the order of steps is exemplary and not limiting.

In step S101, user-target data is received and stored (e.g. in volatile and/or non-volatile computer-readable storage). Typically, the user-target data relates to a selected shade or color—e.g. a user desires to color his/her hair to the selected shade or color. In step S105, characteristic of a user's hair are measured—e.g. using at least a hair-reader device (e.g. for measuring at least one hair-reflection value or for measuring a hair-reflection-spectrum(a)) such as that illustrated in FIG. 2 or 4 or that disclosed in PCT/IB2012/051351 or any related hair-reader device, as discussed below.

In step S117, multi-objective relative importance data is received via hair-treatment objective-prioritization user interface (HTOP UI) 3108—for example, by the user configuring the sliders of FIGS. 5A-5B or in any other manner.

This configures, in step S95, HCC scoring engine 3170 to operate according to the hair-treatment objective-prioritization user interface—e.g. in one non-limiting example, to 'enforce' the alpha coefficients (e.g. EQN1) received via the sliders.

These characteristics received in step S105 may be electronically analyzed in step S109. According to the technique of FIGS. 7A-7B, it is possible to compute a 'customized' hair-treatment that is specific to (i) an initial pre-treatment state of the user's hair (e.g. as measured in step S105 and analyzed in step S109) and (ii) the user-target data.

The term 'user-target' typically or 'target color state' or 'hair-target data' includes to a target color shade—e.g. expressible as a value in color-space such as Hunter Lab color space or any other color space. In addition to a target color shade, user-target data may also include some other desired characteristic of any proposed hair-treatment—e.g. a treatment of 'roots-only' as opposed to 'entire-hair-shaft,' a maximum treatment time, etc.

A plurality of hypothetical or 'candidate' hair-treatment protocols may be analyzed and considered. A 'hair-treatment' may refer to any one of: (A) content of a hair-coloring composition (or more than one hair-coloring composition which may be applied sequentially or simultaneously—for example, a dye-containing composition and a bleaching composition) to be applied to the hair and/or (B) other treatment parameters—e.g. treatment durations, treatment temperature. Computing or specifying a 'hair-treatment' may include specifying at least absolute or relative quantities or 'loads' (i.e. expressed in molar terms, or as weights, or a volumes, or in any other manner known in the art) of one or more hair-coloring agents of a hair-coloring composition (e.g. a 'multi-agent' composition). The term 'hair-coloring agent' may include an artificial colorant/dye, an oxidizer, an alkalizer or an other substance used in the art for temporary, semi-permanent, demi-permanent or permanent hair-coloring. A hair-coloring agent may be in any phase or form, including but not limited to liquid, gel, mouse, cream, solid, powder, tablet, or any other form known in the art. Optionally, a 'hair-treatment' also includes data relating to treatment time, treatment temperature, multi-stage treatments or any other parameter of treatment. For example, a hair-treatment may entail production of multiple distinct combinations of hair-coloring agents—e.g. a coloring mixture and a bleaching mixture which are applied in different stages.

For the present disclosure, the term 'hypothetical' and 'candidate' are used interchangeably and refer to possible treatments that may or may not be actualized.

Typically, the specific characteristics of each user's hair is quite individual (e.g. based upon his/her genotype, age, environmental effects etc.) and the number of potential target shades or colors may also be relatively large. Because of the myriad possible combinations of initial and target hair characteristics, the number of possible candidate/hypothetical hair-treatment protocols may be extremely large, and it is not always known a priori which hair-treatment protocols are predicted to be effective (or most effective) to transform hair from its initial state to a state matching the target data received in step S101.

As such, it may be necessary to electronically analyze multiple hypothetical hair treatments to identify a treatment (or set of more than one hypothetical hair-treatments) which successfully transforms the initial hair to a target color.

This is done in steps S113 and S117. Thus, in step S113, a post-protocol state for the hair is predicted for the hair-characteristics measured in step S105 and a specific candidate hair-treatment. In step S117, a HCC is matched according the customized scoring system It may be electronically determined (i.e. according to the results of the specific scoring) if this post-protocol state matches the specifications of the user target-data.

The term 'hair-color treatment' is not restricted to introducing colorants (e.g. artificial colorants) into the hair (i.e. 'coloring') but may also include hair-bleaching.

In one non-limiting example, (i) in step S105 one or more initial reflection spectrum(a) are measured, (ii) in step S113 a hypothetical post-treatment reflection spectrum is computed from the initial reflection spectrum and specifics of a candidate hair-treatment protocol, and a color value (e.g. an LAB value) is computed from the hypothetical post-treatment reflection spectrum; and (iii) in step S117 this initial-hair-specific and candidate-protocol-specific LAB value is compared to an LAB value associated with the user-target data received in step S101.

In different embodiments, it is possible to measure a reflection spectrum, a transmission spectrum, a spectrum of deflected light, and an absorption spectrum.

In step S121, a protocol that matches the user target-data is selected. Optionally, for example, if more than one candidate protocol matches the user target-data, these candidate protocols may be analyzed and/or scored, and a more preferred matching hair-coloring protocol may be selected accordingly.

In step S125, according to the selected hair-coloring protocol, respective quantities of hair-coloring agent, for a plurality of hair-coloring agents, are each dispensed according to a specifics of the hair-coloring protocol selected in step S121.

One non-limiting example of a dispenser of hair-coloring agents is illustrated in FIG. 11. In this non-limiting example, different respective hair-coloring agents are disposed in each container of a plurality of containers 180A-180Q. In response to the results of step S121, for at least 2 or at least 3 or at least 4 or at least 5 or at least any number of hair-coloring agents, respective quantities of each hair-coloring agent are dispensed into a vessel (not shown) located in port 192.

In some embodiments, the dispenser is automatic and includes electronic circuitry for regulating quantities of hair-coloring agents that are dispensed.

For the present disclosure, a dispensing a plurality of hair-coloring agents according to the results of some sort of computational and/or electronic operation(s) (e.g. a predicting of a post-hypothetical-hypothetical-hair-treatment spectrum (e.g. reflection spectrum) or a color value derived therefrom) refers to one or more of two situations: (i) a situation whereby electronic circuitry automatically controls a dispensing device (the skilled-artisan is directed to PCT/IB2012/051351 incorporated herein by reference) and/or (ii) a situation whereby hair-coloring instructions computed from an electronic predicting is communicated to a human user (e.g. visually via a computer screen or in any other manner). The hair-coloring instructions may relate to relative quantities of hair-coloring agents and the human user follows the instruction to, for example, dispense hair-coloring agent(s) according to the quantities specified by the computer-provided instructions. The container for a chemical agent may have any form factor (e.g. rigid container, tube, etc) and may either may mounted to a dispenser device as illustrated in FIG. 2 or may be a 'free' or unmounted container.

Once these agents are dispensed into the vessel, one or more steps may, optionally, be performed to transform the contents of the vessel (not shown) into a hair-coloring mixture, which may then be applied to the user's hair to color the hair.

For the present disclosures, the terms 'input keratinous fiber(s)' and 'initial hair' are used interchangeably—both refers to keratinous fibers(s) (e.g. hair) which is subjected to one or measurements (e.g. optical measurements and/or reflection measurements—for example, to measure a hair-reflection spectrum(a)) for the purpose of predicting a final state of one or more hypothetical hair-treatments.

The skilled artisan will appreciate that not every step of FIGS. 7A-7B is required in every embodiment, the order of steps of FIGS. 7A-7B is not limiting—the steps may be performed a different order, additional steps may be performed, and one or more steps may be modified.

The following documents are incorporated herein by reference: PCT/IL2014/050850 filed on Sep. 28, 2014 and PCT/IB2015/053065 filed on Apr. 27, 2015.

Definitions

For convenience, in the context of the description herein, various terms are presented here. To the extent that definitions are provided, explicitly or implicitly, here or elsewhere in this application, such definitions are understood to be consistent with the usage of the defined terms by those of skill in the pertinent art(s). Furthermore, such definitions are to be construed in the broadest possible sense consistent with such usage.

A "light detector" or a "detector" refers to one or more photodetectors—e.g. configured as an image sensor and/or in a 1D or 2D array of photodetectors. In another example, a scanning detector apparatus equivalent to a 1D or 2D 'starting' array of photodetectors is used. When light is focused in an image plane at the light detector, the photodetector of the light detector is within the image plane.

The term "color-imparting agent" refers to a hair-coloring agent (e.g. for example, for permanent hair-coloring) or to an ingredient thereof.

A "substantial majority" means at least 75%. In some embodiments, a 'substantial majority' is at least 90% or at least 95% or at least 99%. Unless specified otherwise, a 'majority' means 'at least a majority.' Unless specified otherwise, 'at least a majority' means that, in some embodiments, the 'majority' is at least a substantial majority—i.e. at least 75% or at least 90% or at least 95% or at least 99%.

A 'hair-coloring treatment' is any treatment which modifies the color of hair shafts. Examples of hair-coloring treatments include hair-dying treatments (e.g. based upon artificial colorants) and bleaching. Examples of hair-dying treatments are temporary, demi-permanent, semi-permanent or permanent hair-dying (e.g. oxidative hair-dying).).

An 'initial spectrum' relates to a spectrum before a hair-treatment.

An 'inter-shaft heterogeneity hair parameter,' also referred to as a 'hair heterogeneity parameter, relates to color-property variations (or lack thereof) between individual hair shafts. One example of a 'hair heterogeneity parameter' is the information that a hair sample is 'natural gray hair' or formerly natural gray hair' or 'neither gray hair nor formerly natural gray hair.' Another example of a hair heterogeneity parameter is the fact that a particular hair-sample is a mixture of 25% black hair (i.e. a particular shade of black) and 75% white hair.

For the present disclosure, the term 'shaft' refers to an individual hair and is not limited to the 'shaft portion' (i.e. away from the root portion) of an individual hair.

"Damage' to hair (or 'hair damage') refers to anything that irreversibly changes (i) the mechanical structure or properties of the hair and/or (ii) the chemical status of natural molecules within hair. The "natural molecules" of hair are natural pigments (e.g. melanin species) and proteins of the hair (e.g. fibrous structural proteins such as keratin) that give hair its structure. The "chemical status" of a natural molecule relate to its concentration within the hair or its molecular structure. Examples of irreversibly changing a "chemical status of natural molecules" thus include (i) irreversibly reducing a concentration of a natural pigment (e.g. melanin species) and (ii) irreversibly modifying a molecular structure, for example, by protein denaturation.

A 'damage status' refers to a status of hair reflecting previous damage to the hair.

Causes of 'damage' to hair include but are not limited to exposure to UV light, heating of hair (e.g. during a previous hair-coloring process), exposing hair to dry conditions, mechanical damage (such as combing), exposing hair to chemical materials (such as chlorine) and subjecting hair to a curling treatment.

For the present disclosure, concentration of 'artificial colorants' within the hair are defined as to not relate to the 'damage status' since they do not relate to chemical status of natural molecules or to a mechanical state of the hair. However, dying hair with artificial colorant might cause a certain amount of 'collateral damage.'

The term "color-imparting agent" refers to a hair-coloring agent (e.g. for example, for permanent hair-coloring) or to an ingredient thereof.

A 'hair-coloring treatment' is any treatment which modifies the color of hair shafts. Examples of hair-coloring treatments include hair-dying treatments (e.g. based upon artificial colorants) and bleaching. Examples of hair-dying treatments are temporary, demi-permanent, semi-permanent or permanent hair-dying (e.g. oxidative hair-dying).

The term 'user-target' typically includes to a target color shade—e.g. expressible as a value in color-space such as Hunter Lab color space or any other color space. In addition to a target color shade, user-target data may also include some other desired characteristic of any proposed hair-treatment—e.g. a treatment of 'roots-only' as opposed to 'entire-hair-shaft,' a maximum treatment time, etc.

A plurality of hypothetical or 'candidate' hair-treatment protocols may be analyzed and considered. A 'hair-treatment' may refer to any one of: (A) content of a hair-coloring composition (or more than one hair-coloring composition which may be applied sequentially or simultaneously—for example, a dye-containing composition and a bleaching composition) to be applied to the hair and/or (B) other treatment parameters—e.g. treatment durations, treatment temperature. Computing or specifying a 'hair-treatment' may include specifying at least absolute or relative quantities or 'loads' (i.e. expressed in molar terms, or as weights, or a volumes, or in any other manner known in the art) of one or more hair-coloring agents of a hair-coloring composition (e.g. a 'multi-agent' composition). The term 'hair-coloring agent' may include an artificial colorant/dye, an oxidizer, an alkalizer or an other substance used in the art for temporary, semi-permanent, demi-permanent or permanent hair-coloring. A hair-coloring agent may be in any phase or form, including but not limited to liquid, gel, mouse, cream, solid, powder, tablet, or any other form known in the art. Optionally, a 'hair-treatment' also includes data relating to treatment time, treatment temperature, multi-stage treatments or any other parameter of treatment. For example, a hair-treatment may entail production of multiple distinct combinations of hair-coloring agents—e.g. a coloring mixture and a bleaching mixture which are applied in different stages.

For the present disclosure, the term 'hypothetical' and 'candidate' are used interchangeably and refer to possible treatments that may or may not be actualized.

'Computer storage' refers to computer-readable storage and may be any combination of volatile (e.g. RAM) and/or non-volatile (e.g. flash memory, magnetic medium, optical medium) memory.

An 'immediate' post-treatment state of hair (e.g. color-state) is the predicted state of the hair (i.e. computed by digital computer/electronic circuitry/prediction engine 316) after subjecting the hair to a hair-coloring treatment—e.g. by treating the hair with a hair-coloring composition.

Figure 15:
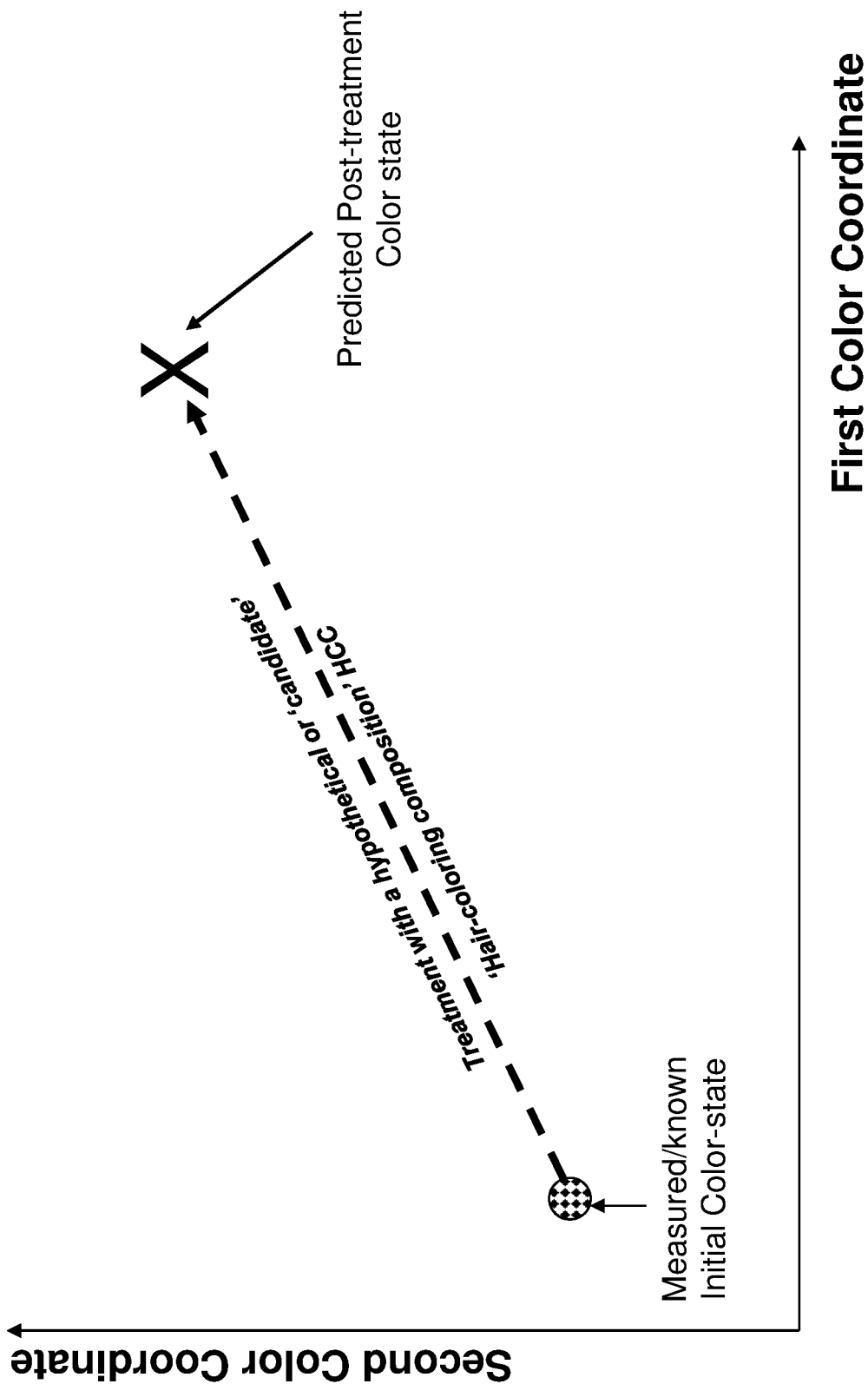

Additional Discussion of FIG. 15

FIG. 15 shows the transformation of hair from an initial color-state to a target color-state (e.g. user-specified) according to a hair-coloring treatment. This transformation may be described in terms of 'change' of coordinates in N-dimensional color hyperspace where N is any positive integer equal to 2 or more—for example, N=3

It is appreciated that when viewed closely, the user's initial hair may include shafts of different color—e.g. a sample of the user's hair may be heterogeneous with respect to color—for example, natural gray hair. Thus, the initial color-state may be a 'representative' color-state of mixture of hair shafts. Similarly, after the hair-coloring treatment not every shaft of hair is required to have the same color—the post-treatment color state (i.e. for which it is desired to be identical to or to approximate the 'target color-state') may also refer to 'representative' color-state of mixture of hair shafts.

The target color-state may be expressed in terms of color-coordinate (e.g. LAB coordinates). It is appreciated that not every hair-coloring treatment succeeds in transforming the user's hair from the initial color-state exactly to the intended target color-state—instead, the result may be an 'approximation' of the target color-state. Thus, embodiments of the present invention relate to transforming a color state of hair from an initial color state to or 'towards' a final color-state (e.g. into a color-state that is substantially identical but not necessarily exactly identical to the final color state). Thus, after hair-coloring treatment (i) the hair is transformed into post-treatment color state; and (ii) a color difference (e.g. expressed as a difference in color hyperspace) between the final color state and the initial color state is greater (e.g. significantly greater) than a difference between the final color state and the post-treatment color state.

In some embodiments, a digital computer may predict the result of a hair-coloring treatment. The result includes a post-treatment color state (e.g. immediately after the hair-coloring treatment and before the hair is subjected to washing(s)). Typically, if there are a plurality of hair-coloring treatments or hair-coloring compositions each treatment (or composition) is associated with a respective predicted post-treatment (e.g. immediate post-treatment) state of the hair including a post-treatment 'color-state' and optionally other post-treatment state information of prediction of which may be computed by the digital computer—e.g. the post-treatment damage state may be predicted.

For example, it is possible to compute a number of 'candidate treatment protocols' and/or 'candidate hair-treatment solutions.' In one example, each of at least some of the containers 180 of the dispenser container a different respective type of solid tablet for oxidative hair-coloring—for example, see PCT/IB2012/051351 filed on Mar. 21, 2012 (incorporated herein by reference in its entirety) and PCT/IL2014/050850 filed on Sep. 28, 2014 (incorporated herein by reference in its entirety). In this example, each candidate solution of a plurality of candidate solutions is associated with numbers of tablets dispensed from each container.

For example, (i) a first candidate solution requires dispensing $x^1_A$ tablets from container 180A, $x^1_B$ tablets from container 180B, $x^1_C$ tablets from container 180C, and so on; (ii) a second candidate solution requires dispensing $x^2_A$ tablets from container 180A, $x^2_B$ tablets from container 180B, $x^2_C$ tablets from container 180C, and so on; (iii) a third candidate solution requires dispensing $x^3_A$ tablets from container 180A, $X^3_B$ tablets from container 180B, $x^3_C$ tablets from container 180C, and so on; (iv) and so on for additional candidate solutions.

According to this 'pure' scoring system based only upon 'immediate-post-treatment color-state accuracy' (see FIGS. 5A and 6A), of the four candidate hair-coloring compositions presented in FIG. 6A, the highest score is assigned to cand2, the next highest score is assigned to cand1, the next highest score is assigned to cand4, and the next highest (and lowest) score is assigned to cand3.

Embodiments of the present invention relate to computing a hair-coloring composition (or associated treatment) according to a merit/scoring system based upon multiple objectives (instead of a 'pure' scoring system based upon the single consideration of immediate-post-treatment color-state accuracy). As will be discussed elsewhere, in some embodiments the merit/scoring function by each which candidate hair-coloring composition (or treatment) is evaluated (e.g. in step S117 or by engine S170) is user configurable via user interface 3108.

Figure 8A:
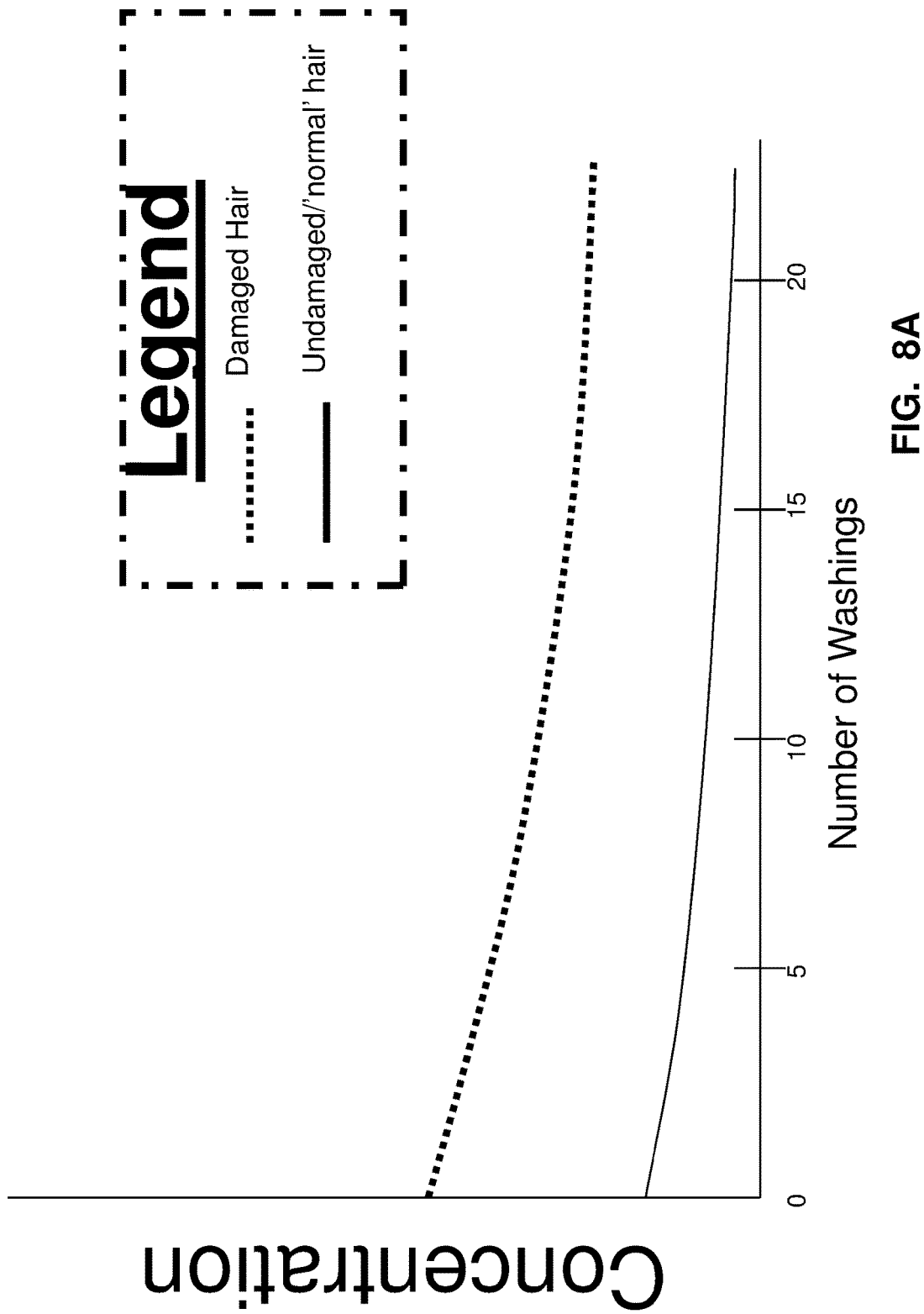

Predicting 'Last'—A Discussion of FIGS. 8A-7C

Figure 8B:
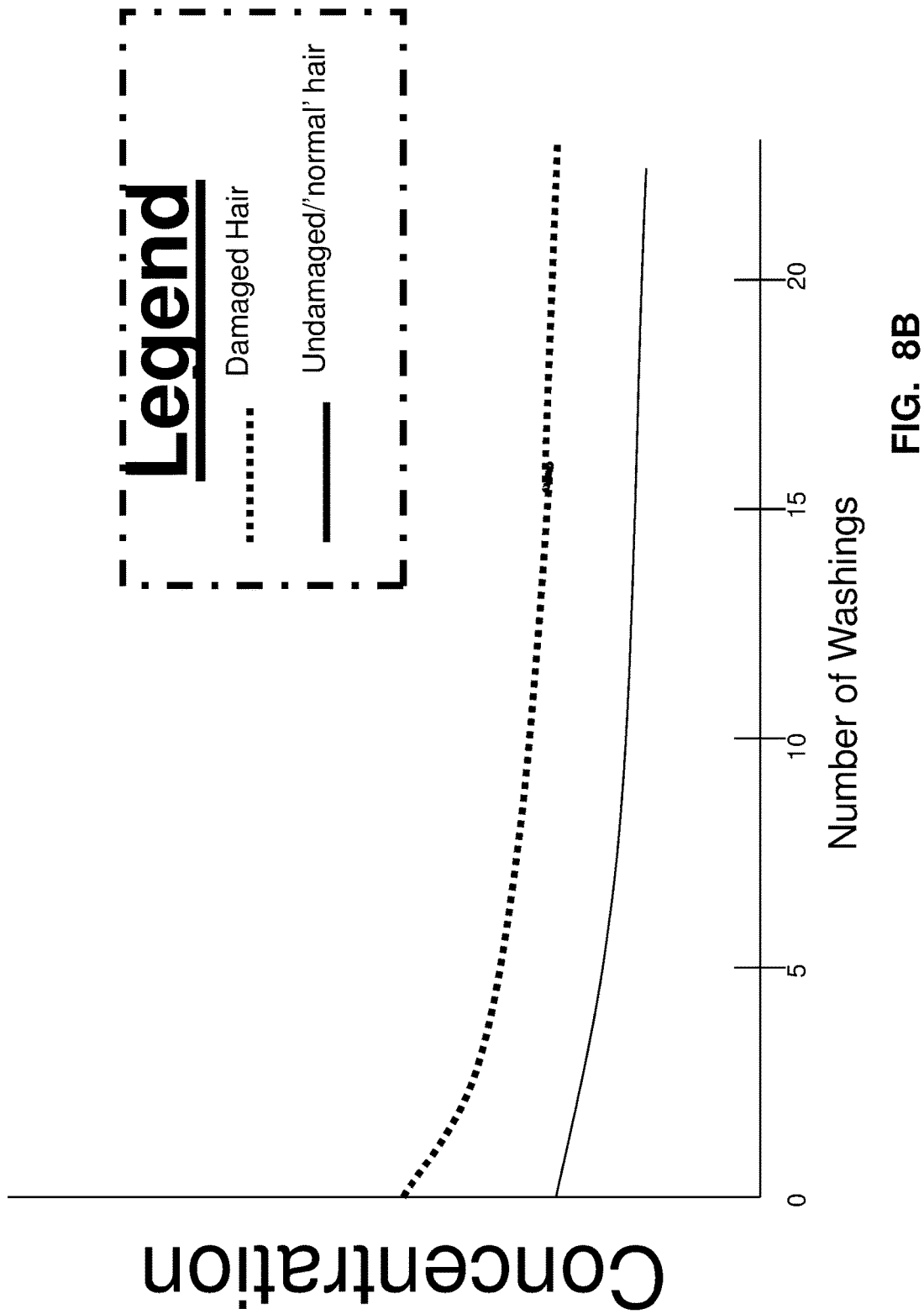

FIG. 8A shows for a 'first artificial colorant' a washing/decay curve—'0' washings shows the immediate post-treatment concentration of the first artificial colorant. The solid curve relates to undamaged or 'normal' hair while the broken curve relates to damaged hair. The term 'decay' relates to the fact that for each washing a certain amount of colorant may be removed from the hair, reducing the concentration. The decay as a function of washings is different for damaged hair and for undamaged hair. FIG. 8A relates to artificial colorant 'A' and FIG. 8B relates to artificial colorant 'B'—inspection of FIGS. 8A-8B shows that the rate of decay is different for different colorants and is different for different damage-states of hair.

As is known in the art (see, for example, PCT/IB2012/051351 filed on Mar. 21, 2012 incorporated by reference), when hair is colored by multiple artificial colorants, it is possible to predict a post-treatment color state by (i) predicting concentrations of each artificial colorant and (ii) converting the concentrations into a color-state. Just as it is possible to predict an immediate post-treatment (i.e. after 'zero' post-treatment washings') state of hair, it is possible using decay curves similar to those of FIGS. 8A-8B to predict the post-treatment state of hair after a specific number of washings. One example is shown in FIG. 7C—the predicted color state of initial hair after hair-coloring treatment (e.g. by a 'candidate composition) is shown. Points 522A, 522B, and 522C are points in color hyperspace describing the color state of the hair respectively (i) immediately after hair-coloring treatment (i.e. after 'zero' subsequent washings)—522A (ii) after '5' subsequent washings—522B and (iii) after '5' subsequent washings—522C.

For a set of artificial colorants, each hair-coloring composition is characterized by different relative concentrations of each artificial colorant. However, just as it is possible to compute an immediate post-treatment color-state of hair, it is also possible to compute post-treatment and post-washing color-state(s) of the hair. Just as it is possible to score a candidate hair-coloring composition or treatment based upon "immediate-post-treatment color-state accuracy" (referred to as "coloring accuracy') it is also possible to score a candidate hair-coloring composition or treatment based upon the post-treatment hair's predicted ability to retain a color-state that is relatively 'close' to the target state even after washing(s)—i.e. the 'robustness' of a 'closeness' between the post-treatment color state and the 'target' color relative to washing.

The candidate hair-coloring composition that achieves the best 'immediate post-treatment' color accuracy is not necessarily the composition whose resulting post-treatment hair retains a color-state 'closely resembling' the target state over time/over post-treatment washes. As such, the color-treatment objective/goals of (i) coloring accuracy for the immediate post-treatment hair and (ii) achieving a color-state which will 'last' or 'be robust' against subsequent post-treatment washing may compete with each other or 'partially contradict each other.'

Figure 8C:
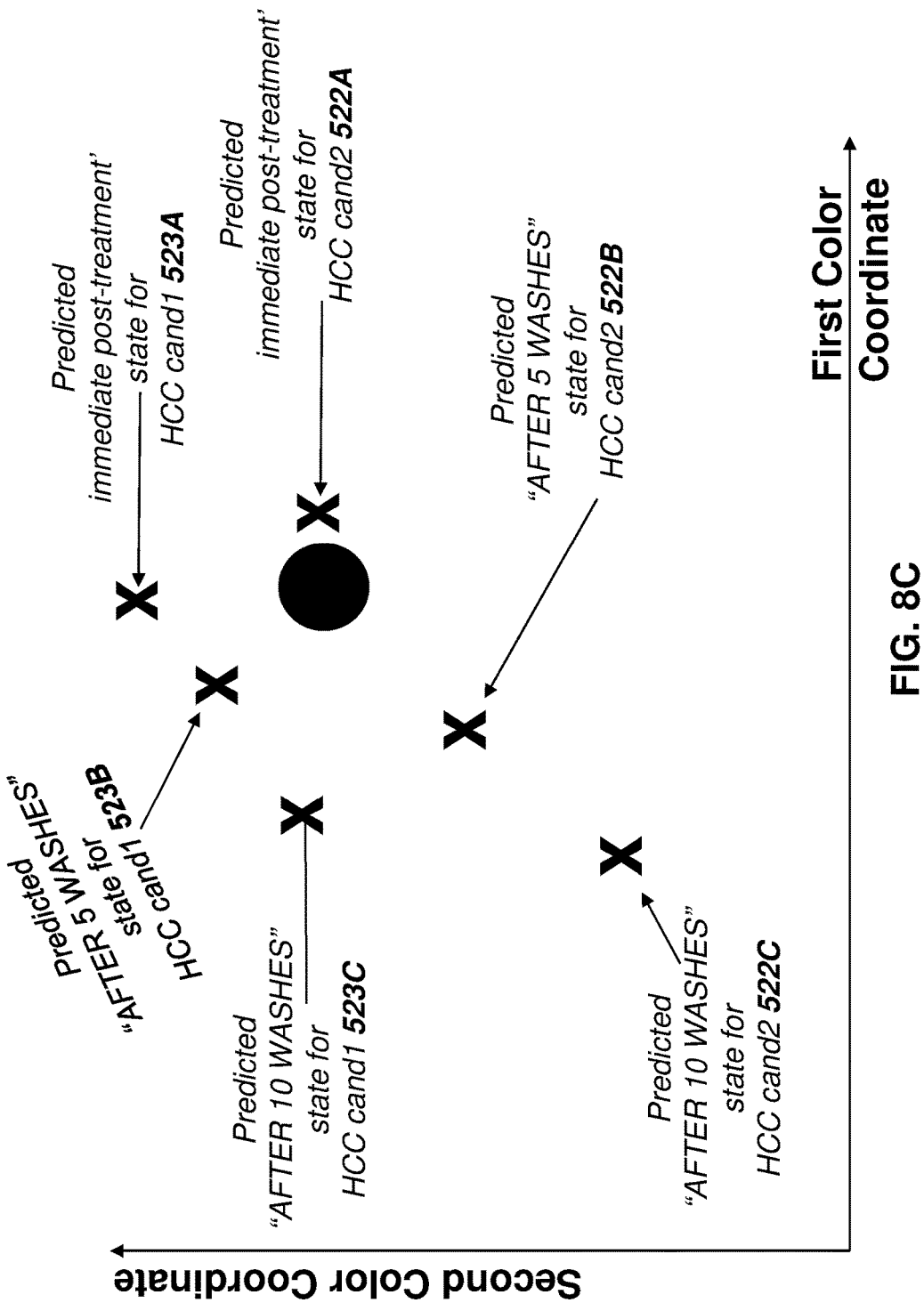

FIG. 8C shows the 'motion' in color space of two post-treatment candidates after washing. For immediate post-treatment accuracy, HCC cand2 is superior to HCC cand1 since point 522A is closer to the target than point 523B. However, after 10 washes the situation references—HCC cand 1 is superior because 523C is closer to the target than 523B.

Predicting 'Hair-Coloring Uniformity—A Discussion of FIGS. 9A-9F

It is appreciated that when viewed closely, the user's initial hair may include shafts of different color—e.g. a sample of the user's hair may be heterogeneous with respect to color—for example, natural gray hair. Thus, the initial color-state may be a 'representative' color-state of mixture of hair shafts. Similarly, after the hair-coloring treatment not every shaft of hair is required to have the same color—the post-treatment color state (i.e. for which it is desired to be identical to or to approximate the 'target color-state') may also refer to 'representative' color-state of mixture of hair shafts.

Coverage/uniformity—as noted above some hair (i.e. natural gray hair but not only natural gray hair) is a mixture of multiple color-types of hair shafts—(i) natural-pigment-containing hair shafts (e.g. melanin-containing hair shafts such as black shafts or red shafts or blond shafts or brown shafts or other natural-pigment-containing shafts) and (ii) natural white hair shafts which are substantially melanin-free. Upon subjecting such hair to a hair-coloring treatment, the post-treatment color-state of the natural-pigment-containing hair shafts may differ from that of the natural white hair shafts—see PCT/IB2015/000724 filed on Mar. 25, 2015 incorporated herein by reference which discloses techniques for computing the respective post-treatment color-state of each type of hair-shaft. The greater the (predicted) color-deviation between the different types of hair-shafts the lower the (predicted) 'coverage/uniformity'—the lower the (predicted) color-deviation between the different types of hair-shafts the greater the (predicted) 'coverage/uniformity.'

Figure 9A:
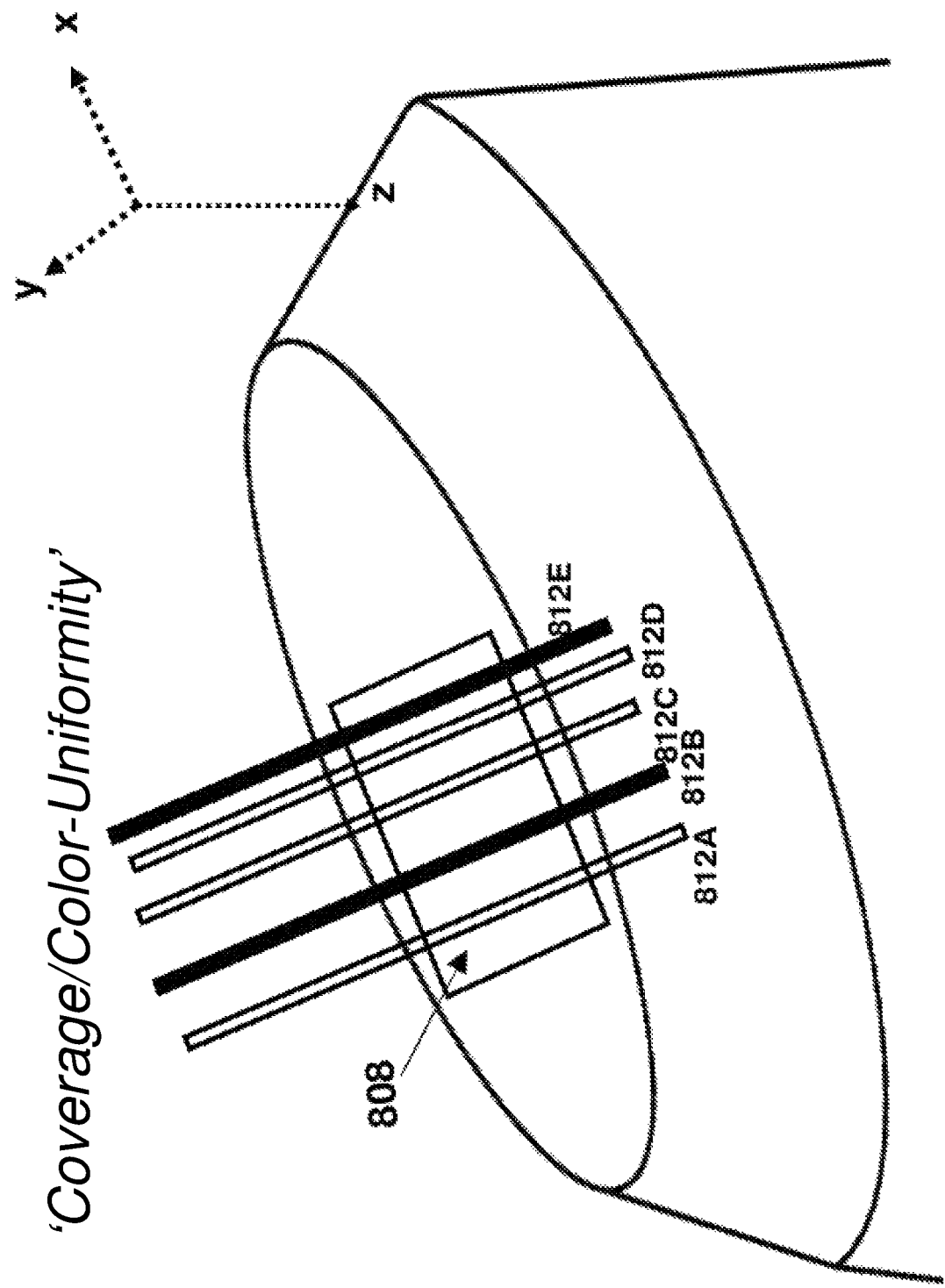

FIG. 9A illustrates an example of a color-heterogeneous mixture of hair-shafts—instead of only predicting a final color state of the mixture as a whole, it is possible to compute first and second predicted post-treatment color states respectively for the first (e.g. pigment-containing) and second (e.g. natural-weight) initial hair—the skilled artisan is directed to PCT/IB2015/000724. Once these predicted post-treatment color-states are computed, it is possible to compute a 'color-difference' (e.g. distance in color hyperspace) therebetween to characterize a uniformity/coverage of the candidate hair-coloring treatment.

Figure 9B:
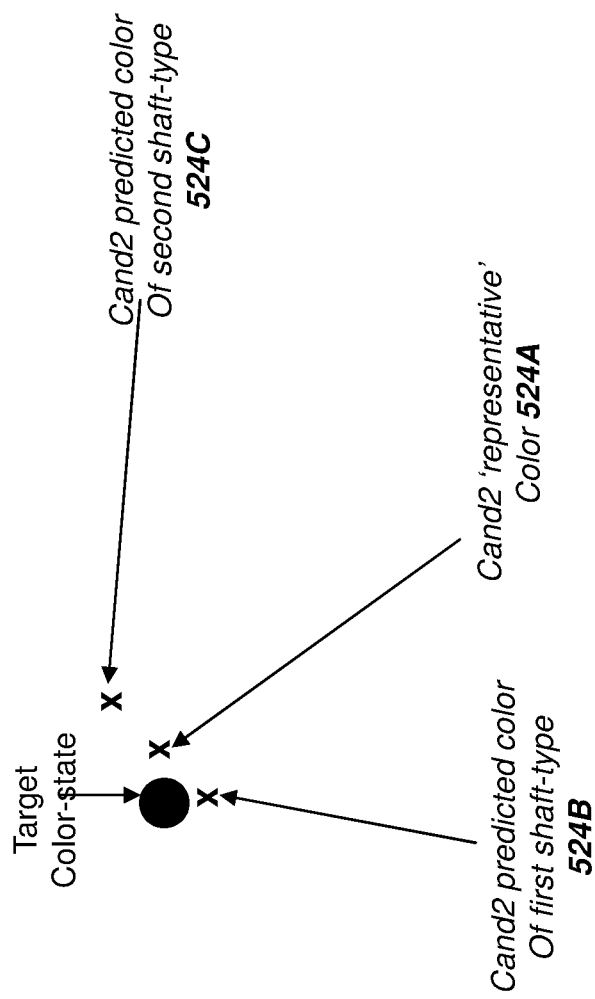

FIG. 9B illustrates points in color-state hyperspace (e.g. LAB space) related to predicted color-states of a color-heterogeneous mixture of hair-shafts after subjecting the mixture of hair-shafts to a candidate color-treatment or treating with a candidate hair-composition. In particular, FIG. 8B illustrates the following points in color-state hyperspace—(i) the predicted (e.g. as computed by prediction engine) color state 524B of hair-shafts of 'the first type' after a candidate hair-coloring treatment by a hair-coloring composition cand2; (ii) the predicted (e.g. as computed by prediction engine) color state 524C of hair-shafts of 'the second type' after a candidate hair-coloring treatment by a hair-coloring composition cand2; (iii) the predicted (e.g. as computed by prediction engine) 'overall' mixture-averaged color state 524A of the color-heterogeneous mixture of hair-shafts of hair after a candidate hair-coloring treatment by a hair-coloring composition cand2 which may be a weighted average (i.e. weighted by relative quantities of hair shafts of the first and second type—e.g. natural-pigment containing and natural-white).

The greater the distance between points 524B and 524C (or between 524A and 524B or between 524A and 524C) the lower the 'uniformity' or coverage. Conversely, the greater the distance between points 524B and 524C (or between 524A and 524B or between 524A and 524C) the lower the 'uniformity' or coverage.

Similar to the situation with the goals of 'color accuracy' and 'last', the goals of coloring accuracy and coverage/uniformity may be competing goals. Also, the goals of 'last' and 'coverage/uniformity' may also be competing goals.

In the example 9C-9D, HCC cand1 is analyzed for initial hair that is heterogeneous with respect to color. In the example 9E-9F, HCC cand2 is analyzed for initial hair that is heterogeneous with respect to color.

For the present disclosure, immediate post-treatment color state represents to the state representative for the hair as a whole, unless specified otherwise, rather than for a type of constitutive hair shaft (e.g. for hair that is color-heterogeneous with respect to shaft color—e.g. natural gray hair).

Figure 9C:
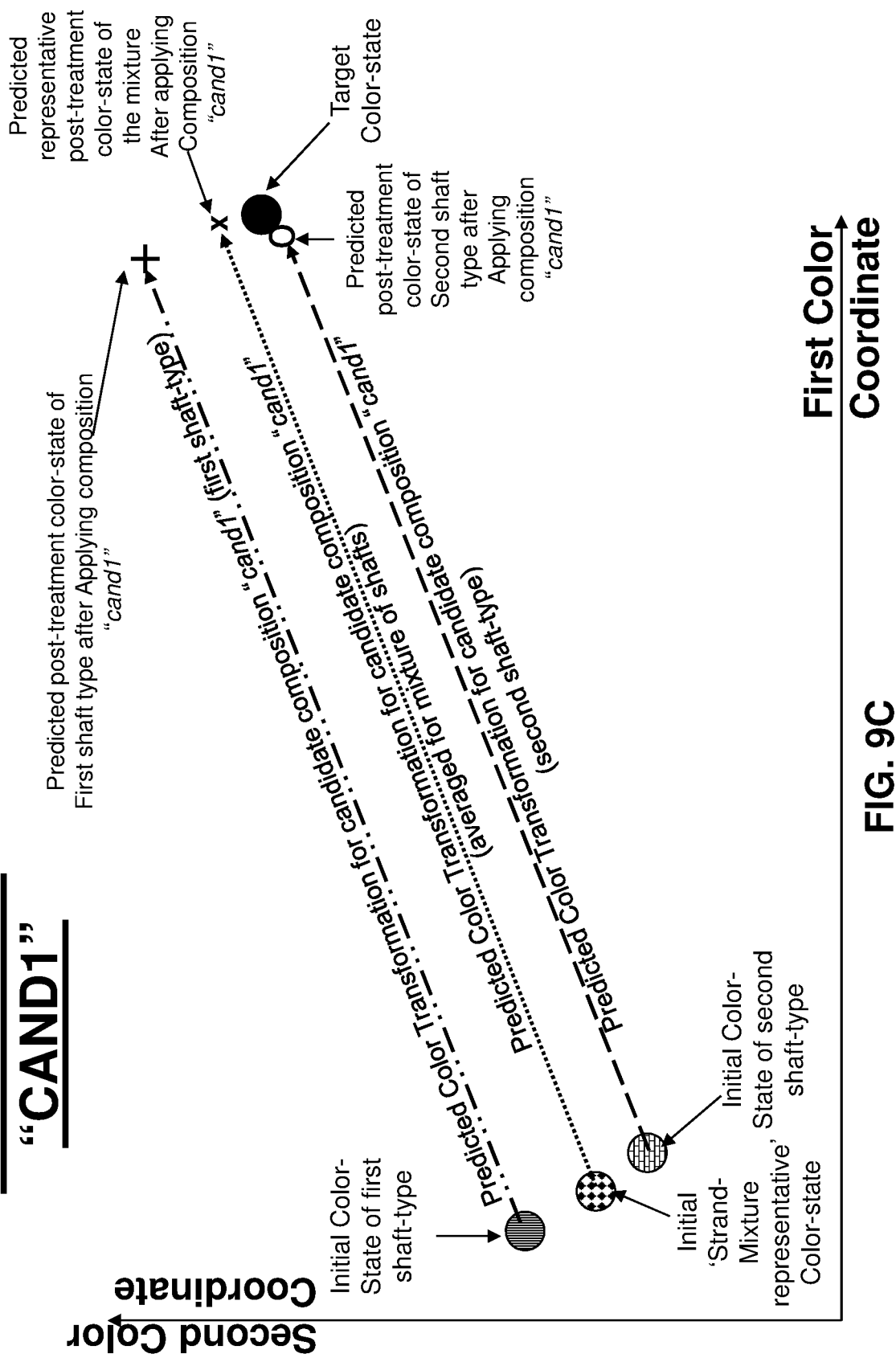
Figure 9D:
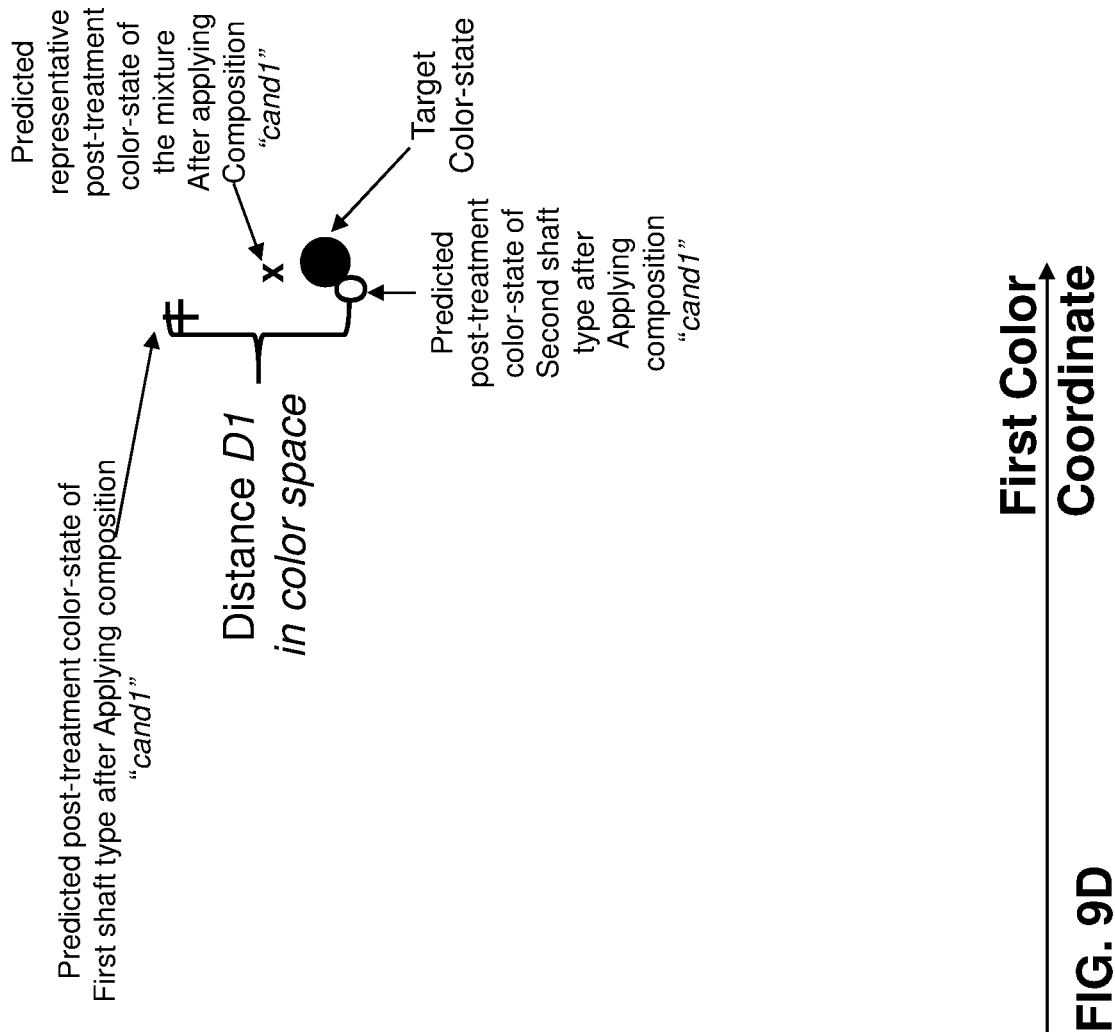
Figure 9D:
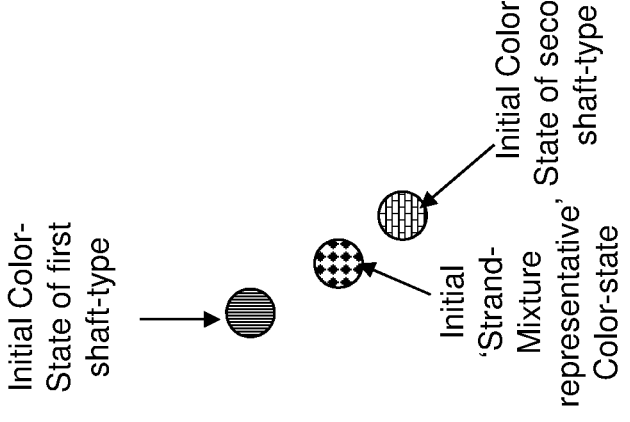
Figure 9E:
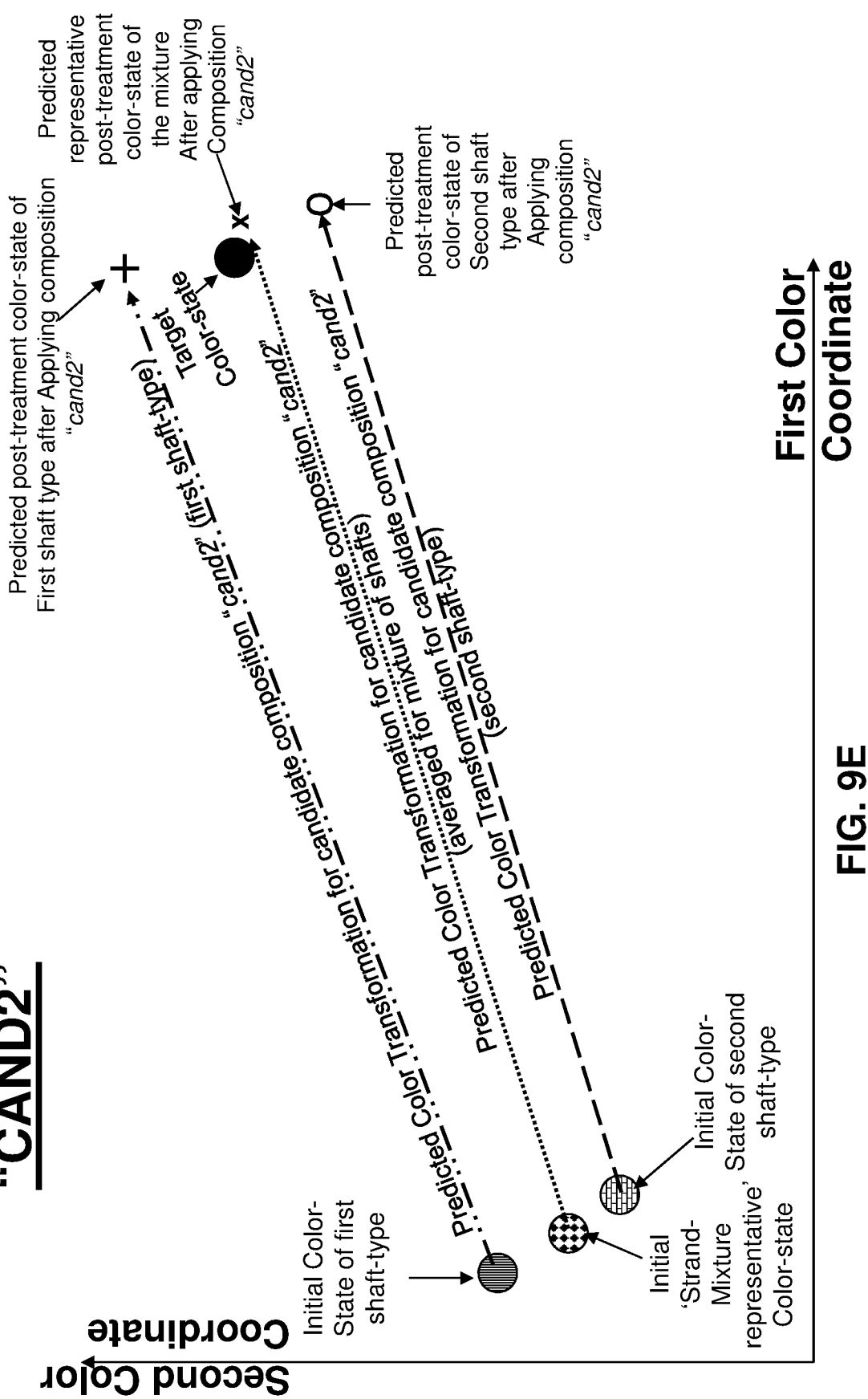

In the examples of FIGS. 9C and 9E, the "x" represents the immediate post-treatment color state which is closer to the target in FIG. 9C than in FIG. 9E, indicating that HCC cand1 is predicted to have better immediate post-treatment accuracy than HCC cand2.

Figure 9F:
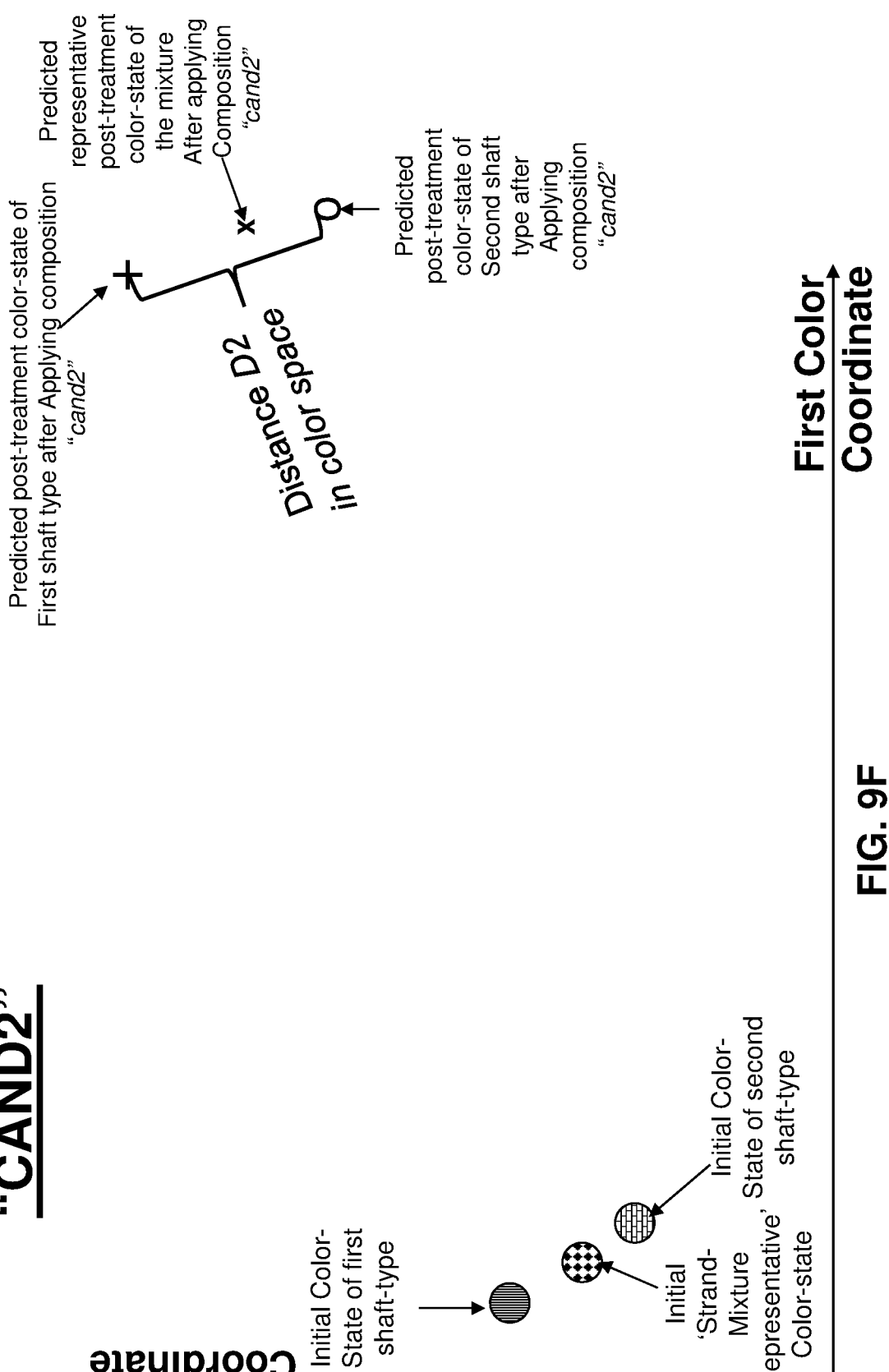

However, the predicted color uniformity of HCC cand2 is better, as observed FIGS. 9D and 9F where the distance D1 is less than the distance D2.

A Discussion of Gentleness/Damage

In some embodiments, it is desired to provide a hair-coloring treatment that minimizes the predicted post-treatment damage state of hair and/or that ensures that the predicted post-treatment damage state does not exceed a maximum threshold. Towards this end, it is useful to measure the initial damage of the hair. The predicted post-treatment damage-state of hair is a function of (i) the initial damage-state of the hair and (ii) the predicted-damage inflicted upon the hair by the hair-coloring treatment (e.g. this may depend upon concentrations of oxidizing agent(s) (e.g. peroxide) and/or alkalizing agent(s) (e.g. ammonia) and/or upon other factors.

Techniques for measuring an initial damage state of hair are described in PCT/IB2015/053065 filed on Apr. 27, 2015—also see FIGS. 13A-13B and 14A-14B. It is possible to subject aligned hair-shafts to two measurements (e.g. in configurations shown in FIGS. 13A-13B and 14A-14B) and to compare the intensity of light scattered by the aligned hair-shafts illuminated by light-beams from different directions (e.g. directions 1020A and 1020B of FIG. 13A or directions 1020C and 1020D of FIG. 13B). e.g. when the intensity of scattered light is similar this may be indicative of a greater damage state.

As evident from the curves of FIGS. 8A-8B, measurement of initial hair damage may also be useful for predicting 'last.'

Figure 10A:
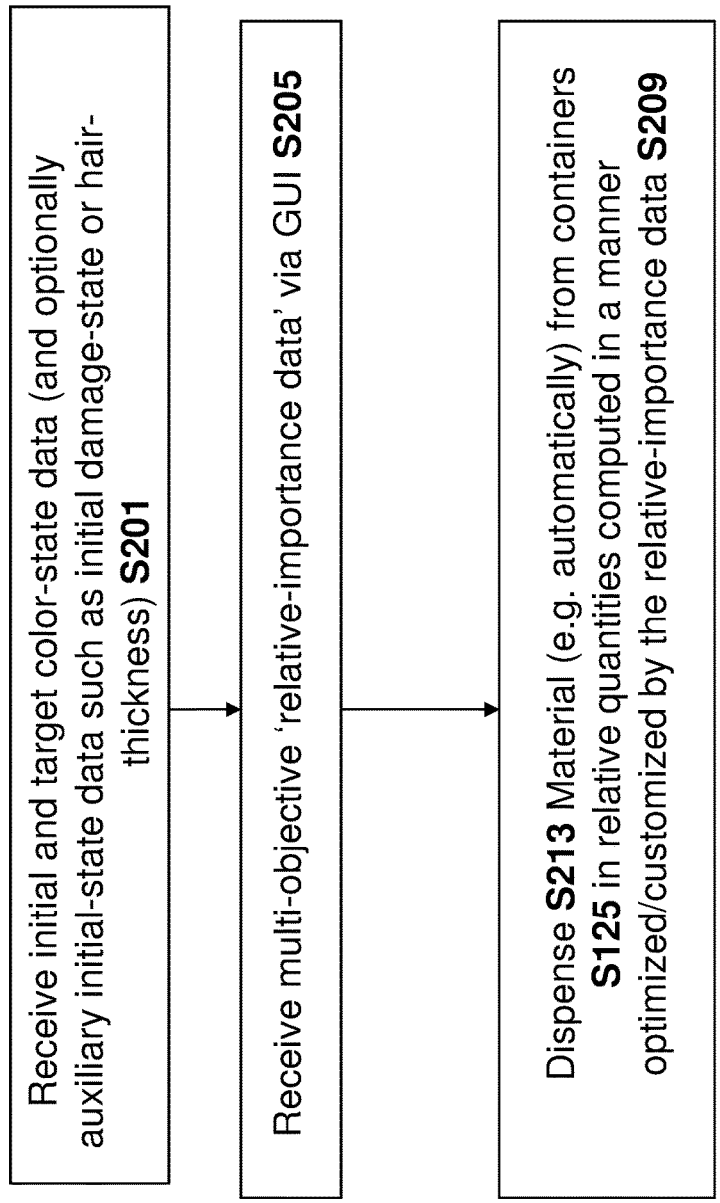
Figure 10B:
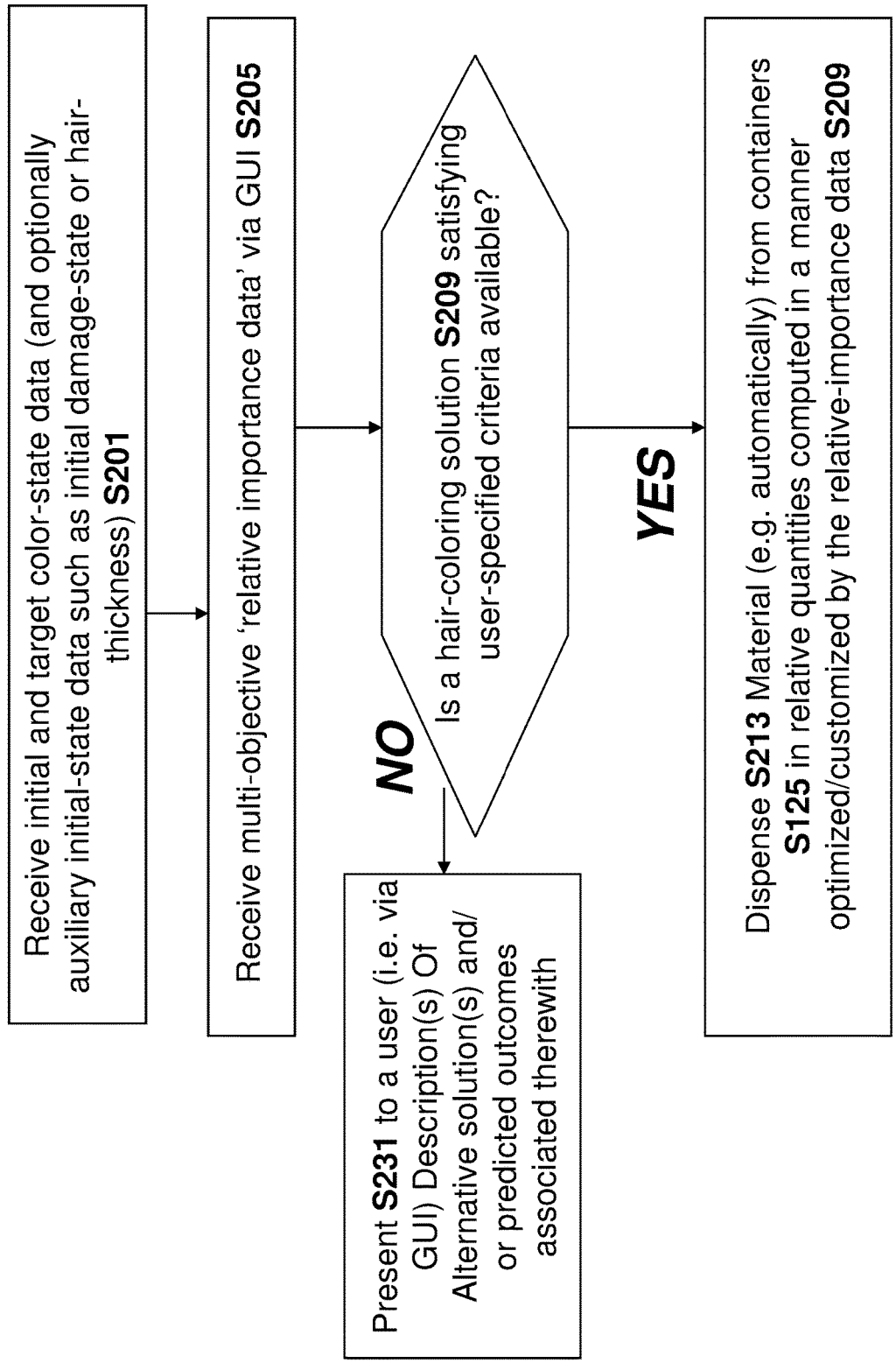
Figure 10C:
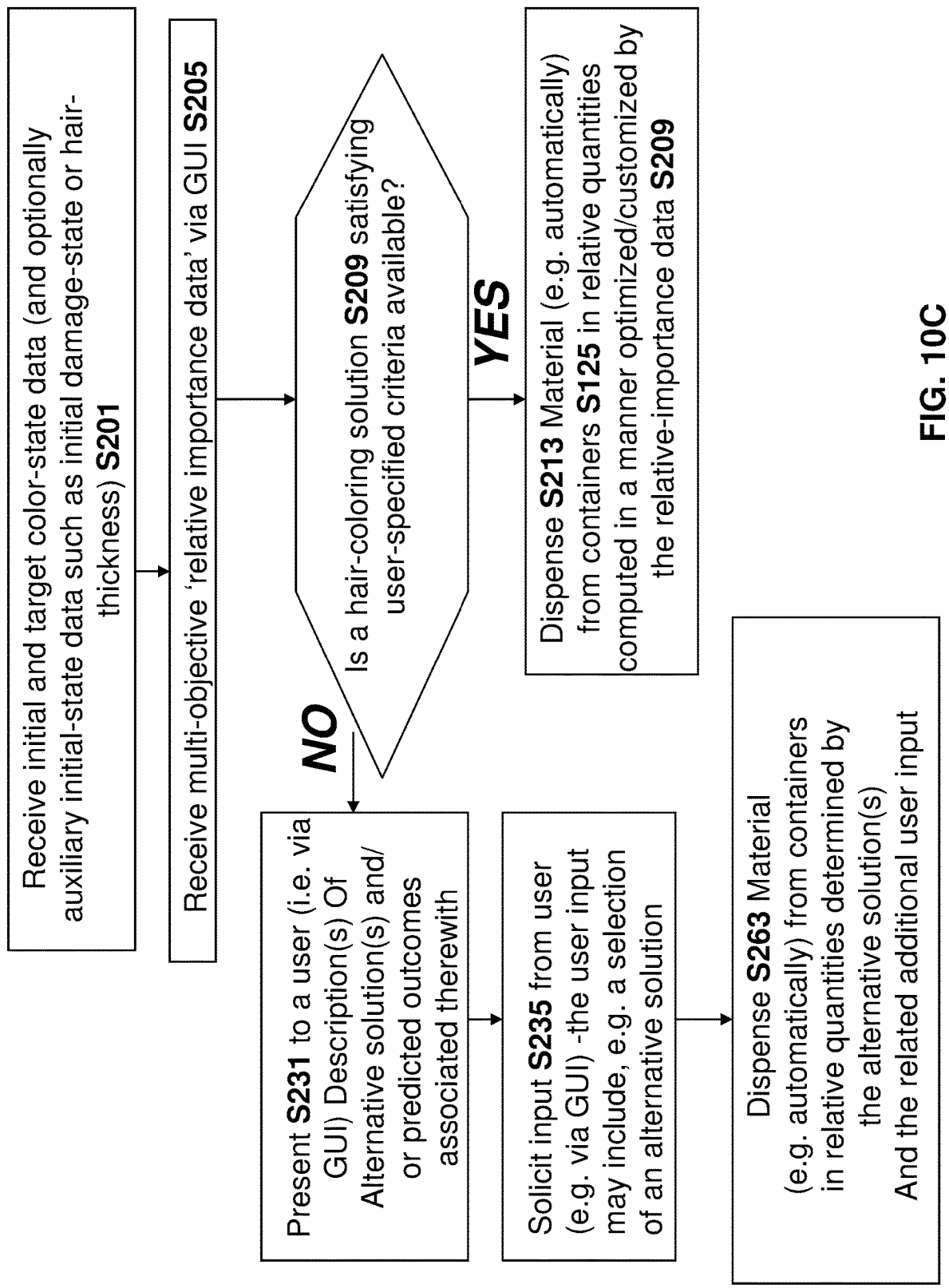

A Discussion of FIGS. 10A-10C

FIGS. 10A-10C show related methods useful for gentleness—these methods may be used also for additional auxiliary objectives. In some embodiments, it (see step S209) in accordance with the user-provided (i.e. via the user interface) multi-objective relative-important data (e.g. relative importance of last vs. color accuracy, color vs. damage, uniformity vs. color accuracy, uniformity vs. last, etc or any combination), it may be decided that no solution is available—according to the user-specific multi-objective relative-important data (e.g. provided by the sliders of FIGS. 9A-9B)—i.e. in step S209 no solution may be 'available'—this means in general or according to the materials present within the containers of the dispenser. In this situation, an alternative solution(s) may be presented (steps S231) to the user (e.g. at least some aspect of each alternative solution—e.g. a description of its predicted immediate post-treatment color) and optionally input may be solicited in step S235.

A system for preparing a customized hair-coloring composition by dispensing material, the system comprises: a hair-state circuit configured to store a target color state for the potential hair-coloring treatment and initial hair-state data describing at least an initial color-state of the user's hair before being subjected to the potential hair-coloring treatment, the hair-state circuit further configured to store an auxiliary-objective rule describing achieving an auxiliary objective (e.g. stored in any volatile or non-volatile storage/memory); a hair-coloring-composition (HCC) prediction-engine configured to compute, from the initial hair-state data and from the target color-state, a customized hair-coloring composition predicted to transform a color state of the user's hair from the initial color state to the target color state; and a HCC user interface (HCC UI) comprising a recommendation-presentation user interface RP UI for presenting recommendations about the computed HCC or about target color-states; wherein: the HCC prediction-engine determines (e.g. see step S209 of FIGS. 10B-10C) an existence of an auxiliary-objective rule-compliant HCC predicted to transform the color state to the target color state without violating the auxiliary-objective rule; in the computed absence of an auxiliary-objective rule-compliant HCC, the hair-coloring-composition (HCC) prediction-engine computes an alternative HCC predicted to comply with the auxiliary-objective rule at the expense of predicted immediate-post-treatment color-state accuracy; in the computed absence (e.g. see no branch leaving S209) of an auxiliary-objective rule-compliant HCC, the RP UI responds by announcing (e.g. see S231) the computed absence and/or by presenting the auxiliary-objective rule-compliant alternative HCC.

In some embodiments, further comprising: a dispenser device having a plurality of containers, a different material being respectively disposed in each container, the dispenser device configured to respectively dispense a different quantity of material from each container in response to and according to computations performed by the hair-coloring-composition (HCC) prediction-engine.

In some embodiments, if such an auxiliary-objective rule-compliant HCC exists, the system responds by performing at least one of the following i. the HCC UI responds by announcing an existence of the auxiliary-objective rule-compliant HCC; and ii. the dispenser devices dispenses material from the container at relative quantities determined by the HCC predict-engine for the auxiliary-objective rule-compliant HCC.

In some embodiments, the auxiliary-objective rule is a maximum-damage-rule limiting an amount of predicted post-hair-coloring-treatment damage of the hair.

In some embodiments, the auxiliary-objective rule is wash-robustness-rule requiring a predicted color-retention against post-coloring washing.

In some embodiments, the auxiliary-objective rule is predicted hair-color-uniformity rule describing a predicted hair-color uniformity among different-colored shafts of the initial pre-coloring hair.

In the description and claims of the present application, each of the verbs, "comprise" "include" and "have", and conjugates thereof, are used to indicate that the object or objects of the verb are not necessarily a complete listing of members, components, elements or parts of the subject or subjects of the verb.

All references cited herein are incorporated by reference in their entirety. Citation of a reference does not constitute an admission that the reference is prior art.

The articles "a" and "an" are used herein to refer to one or to more than one. (i.e., to at least one) of the grammatical object of the article. By way of example, "an element" means one element or more than one element.

The term "including" is used herein to mean, and is used interchangeably with, the phrase "including but not limited" to.

The term "or" is used herein to mean, and is used interchangeably with, the term "and/or," unless context clearly indicates otherwise.

The term "such as" is used herein to mean, and is used interchangeably, with the phrase "such as but not limited to".

Having thus described the foregoing exemplary embodiments it will be apparent to those skilled in the art that various equivalents, alterations, modifications, and improvements thereof are possible without departing from the scope and spirit of the claims as hereafter recited. In particular, different embodiments may include combinations of features other than those described herein. Accordingly, the claims are not limited to the foregoing discussion.

What is claimed is:

1. A system for preparing a customized hair-coloring composition by dispensing material, the system comprising:
   a hair-treatment objective-prioritization user interface (HTOP UI) for receiving multi-objective relative-importance data describing a relative importance of different hair-treatment objectives for a potential hair-coloring treatment;
   a hair-state circuit configured to store a target color state for the potential hair-coloring treatment and initial hair-state data describing at least an initial color-state of the user's hair before being subjected to the potential hair-coloring treatment; and
   a hair-coloring-composition (HCC) prediction-engine responsive to input received via the HTOP UI, the hair-coloring-composition prediction-engine configured to compute, from the initial hair-state data and from the target color-state, a customized hair-coloring composition predicted to transform a color state of the user's hair from the initial color state to the target color state;
   wherein:
      the HTOP UI is configured so that the multi-objective relative-importance data describes a relative importance of (A) reaching the target color-state; and (B) achieving at least one auxiliary objective(s) or achieving a user-specified weighted combination of auxiliary objective(s);
      in response to receipt, via the HTOP UI, of multi-objective relative-importance data that prioritizes immediate-post-treatment color-state accuracy at the expense of achieving the auxiliary objective, the HCC prediction-engine computes a hair-coloring composition predicted to more accurately transform the user's hair to the target color state at the expense of achieving the auxiliary objective; and
      in response to receipt, via the HTOP UI, of multi-objective relative-importance data that prioritizes achieving the auxiliary objective at the expense of predicted immediate-post-treatment color-state accuracy, the HCC prediction-engine computes a hair-coloring composition that achieves the auxiliary objective at the expense of immediate-post-treatment color-state accuracy.

2. The system of claim 1, wherein at least one of the auxiliary objectives is post-treatment color-retaining wash-robustness.

3. The system of claim 1, wherein at least one of the auxiliary objectives is achieving uniform color-state between initial hair-shafts of different colors.

4. The system of claim 1, wherein at least one of the auxiliary objectives is minimizing a post-treatment damage state and/or predicting that the post-treatment damage state does not exceed a threshold.

5. The system of claim 1, wherein at least one of the auxiliary objectives is minimizing a treatment complexity.

6. The system of claim 1 wherein the target color state and/or the initial hair-state data comprises at least one of spectral data and colorimetric data.

7. The system of claim 6 wherein the spectral data comprises at least one of a reflection spectrum, a transmission spectrum and an absorption spectrum.

8. A system for preparing a customized hair-coloring composition by dispensing material, the system comprising:
 a hair-treatment objective-prioritization user interface (HTOP UI) for receiving multi-objective relative-importance data describing a relative importance of different hair-treatment objectives for a potential hair-coloring treatment;
 a hair-state circuit configured to store a target color state for the potential hair-coloring treatment and initial hair-state data describing at least an initial color-state of the user's hair before being subjected to the potential hair-coloring treatment; and
 a hair-coloring-composition (HCC) prediction-engine responsive to input received via the HTOP UI, the hair-coloring-composition prediction-engine configured to compute, from the initial hair-state data and from the target color-state, a customized hair-coloring composition predicted to transform a color state of the user's hair from the initial color state to the target color state;
wherein:
 the HTOP UI is configured so that the multi-objective relative-importance data describes a relative importance of (A) reaching the target color-state; and (B) achieving at least one auxiliary objective(s) or achieving a user-specified weighted combination of auxiliary objective(s);
 in response to receipt, via the HTOP UI, of multi-objective relative-importance data that prioritizes the first auxiliary objective the expense of the second auxiliary objective, the hair-coloring-composition (HCC) prediction engine computes a hair-coloring composition that is predicted to achieve the first auxiliary objective at the expense of the second auxiliary objective; and
 in response to receipt, via the HTOP UI, of multi-objective relative-importance data that prioritizes the second auxiliary objective the expense of the first auxiliary objective, the hair-coloring-composition (HCC) prediction engine computes a hair-coloring composition that is predicted to achieve the second auxiliary objective at the expense of the first auxiliary objective.

* * * * *